US010969392B2

(12) United States Patent
Balko et al.

(10) Patent No.: US 10,969,392 B2
(45) Date of Patent: Apr. 6, 2021

(54) METHODS AND SYSTEMS FOR PREDICTING RESPONSE TO IMMUNOTHERAPIES FOR TREATMENT OF CANCER

(71) Applicant: Vanderbilt University, Nashville, TN (US)

(72) Inventors: Justin M. Balko, Brentwood, TN (US); Douglas B. Johnson, Nashville, TN (US); Violeta Sanchez de Delgado, Nashville, TN (US); Melinda Sanders, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 669 days.

(21) Appl. No.: 15/376,276

(22) Filed: Dec. 12, 2016

(65) Prior Publication Data

US 2017/0168054 A1 Jun. 15, 2017

Related U.S. Application Data

(60) Provisional application No. 62/265,714, filed on Dec. 10, 2015.

(51) Int. Cl.
| | |
|---|---|
| *A61K 39/395* | (2006.01) |
| *G01N 33/574* | (2006.01) |
| *A61K 31/416* | (2006.01) |
| *C07K 16/28* | (2006.01) |
| *A61K 38/45* | (2006.01) |
| *A61K 31/166* | (2006.01) |
| *A61K 31/44* | (2006.01) |
| *A61K 31/4523* | (2006.01) |
| *A61K 31/519* | (2006.01) |
| *A61K 31/4412* | (2006.01) |
| *G01N 33/569* | (2006.01) |
| *A61K 39/00* | (2006.01) |

(52) U.S. Cl.
CPC ....... *G01N 33/5743* (2013.01); *A61K 31/166* (2013.01); *A61K 31/416* (2013.01); *A61K 31/44* (2013.01); *A61K 31/4412* (2013.01); *A61K 31/4523* (2013.01); *A61K 31/519* (2013.01); *A61K 38/45* (2013.01); *C07K 16/2818* (2013.01); *C07K 16/2833* (2013.01); *G01N 33/56977* (2013.01); *G01N 33/57407* (2013.01); *A61K 2039/505* (2013.01); *G01N 2333/70539* (2013.01)

(58) Field of Classification Search
None
See application file for complete search history.

(56) References Cited

U.S. PATENT DOCUMENTS

2003/0138862 A1* 7/2003 Tso .................... C07K 16/2833
435/7.23

FOREIGN PATENT DOCUMENTS

| WO | WO2015/051320 | * | 4/2015 |
| WO | WO2016/196389 | * | 12/2016 |

OTHER PUBLICATIONS

De Genst et al., Dev Comp Immunol; 30:187-98 (Year: 2006).*
Almagro & Fransson, Frontiers in Bioscience 2008; 13:1619-33 (Year: 2008).*
Yoshinaga et al., J. Biochem 2008; 143:593-601 (Year: 2008).*
Topalian, S.L., et al. Safety, activity, and immune correlates of anti-PD-1 antibody in cancer. The New England journal of medicine 366, 2443-2454 (2012).
Hamid, O., et al. Safety and Tumor Responses with Lambrolizumab (Anti-PD-1) in Melanoma. The New England journal of medicine 369, 134-144 (2013).
Herbst, R.S., et al. Predictive correlates of response to the anti-PD-L1 antibody MPDL3280A in cancer patients. Nature 515, 563-567 (2014).
Robert, C., et al. Nivolumab in Previously Untreated Melanoma without BRAF Mutation. The New England journal of medicine (2014).
Robert, C., et al. Anti-programmed-death-receptor-1 treatment with pembrolizumab in ipilimumab-refractory advanced melanoma: a randomised dose-comparison cohort of a phase 1 trial. Lancet (2014).
Robert, C., et al. Pembrolizumab versus Ipilimumab in Advanced Melanoma. The New England journal of medicine (2015).
Rizvi, N.A., et al. Activity and safety of nivolumab, an anti-PD-1 immune checkpoint inhibitor, for patients with advanced, refractory squamous non-small-cell lung cancer (CheckMate 063): a phase 2, single-arm trial. The lancet oncology 16, 257-265 (2015).
Garon, E.B., et al. Pembrolizumab for the Treatment of Non-Small-Cell Lung Cancer. The New England journal of medicine (2015).
Gettinger, S.N., et al. Overall Survival and Long-Term Safety of Nivolumab (Anti-Programmed Death 1 Antibody, BMS-936558, ONO-4538) in Patients With Previously Treated Advanced Non-Small-Cell Lung Cancer. Journal of clinical oncology : official journal of the American Society of Clinical Oncology (2015).

(Continued)

*Primary Examiner* — Meera Natarajan
(74) *Attorney, Agent, or Firm* — Stites & Harbison PLLC; Summer E. Young; Mandy Wilson Decker

(57) ABSTRACT

A method of detecting cell membrane expression of an MHC molecule in a subject, a method of treating cancer in a subject with an immunotherapeutic agent, and an MHC complex are provided. The method of detecting cell membrane expression of an MHC molecule includes obtaining a tumor cell sample from a subject, and detecting cell membrane expression of the MHC molecule by contacting the tumor cell sample with an antibody targeting the MHC molecule and detecting binding between the MHC molecule and the antibody. The method of treating cancer in a subject with an immunotherapeutic agent includes detecting cell membrane expression of an MHC molecule in the subject and administering a therapeutically effective amount of the immunotherapeutic agent if the level of cell membrane expression of the MHC molecule exceeds a predetermined standard. The complex includes a tumor cell in complex with an antibody or an antigen-binding portion thereof.

10 Claims, 23 Drawing Sheets

(56) References Cited

OTHER PUBLICATIONS

Motzer, R.J., et al. Nivolumab for Metastatic Renal Cell Carcinoma: Results of a Randomized Phase II Trial. Journal of clinical oncology : official journal of the American Society of Clinical Oncology (2014).
Powles, T., et al. MPDL3280A (anti-PD-L1) treatment leads to clinical activity in metastatic bladder cancer. Nature 515, 558-562 (2014).
Ansell S.M., et al. PD-1 Blockade with Nivolumab in Relapsed or Refractory Hodgkin's Lymphoma. The New England journal of medicine (2014).
Nanda R. Chow LQ, Dees EC, Berger R, Gupta S, et al. A phase Ib study of pembrolizumab (MK-3475) in patients with advanced triple-negative breast cancer. in San Antonio Breast Cancer Symposium (2014).
Seiwert, T.Y., Burtness B, Weiss J, Gluck I, Eder JP, et al. A phase Ib study of MK-3475 in patients with human papillomavirus (HPV)-associated and non-HPV-associated head and neck (H/N) cancer. Journal of clinical oncology : official journal of the American Society of Clinical Oncology 32, 6011 (2014).
Brahmer, J.R., et al. Phase I study of single-agent anti-programmed death-1 (MDX-1106) in refractory solid tumors: safety, clinical activity, pharmacodynamics, and immunologic correlates. Journal of clinical oncology : official journal of the American Society of Clinical Oncology 28, 3167-3175 (2010).
Snyder, A., et al. Genetic Basis for Clinical Response to CTLA-4 Blockade in Melanoma. The New England journal of medicine (2014).
Yadav, M., et al. Predicting immunogenic tumour mutations by combining mass spectrometry and exome sequencing. Nature 515, 572-576 (2014).
Tumeh, P.C., et al. PD-1 blockade induces responses by inhibiting adaptive immune resistance. Nature 515, 568-571 (2014).
Spranger, S., Bao, R. & Gajewski, T.F. Melanoma-intrinsic beta-catenin signalling prevents anti-tumour immunity. Nature 523, 231-235 (2015).
Mellman, I., Coukos, G. & Dranoff, G. Cancer immunotherapy comes of age. Nature 480, 480-489 (2011).
Mikucki, M.E., et al. Non-redundant requirement for CXCR3 signalling during tumoricidal T-cell trafficking across tumour vascular checkpoints. Nat Commun 6, 7458 (2015).
Garrido, F., Cabrera, T. & Aptsiauri, N. "Hard" and "soft" lesions underlying the HLA class I alterations in cancer cells: Implications for immunotherapy. Int J Cancer 127, 249-256 (2010).
Warabi, M., Kitagawa, M. & Hirokawa, K. Loss of MHC class II expression is associated with a decrease of tumor-infiltrating T cells and an increase of metastatic potential of colorectal cancer: immunohistological and histopathological analyses as compared with normal colonic mucosa and adenomas. Pathol Res Pract 196, 807-815 (2000).
Bernsen, M.R., et al. On the biological relevance of MHC class II and B7 expression by tumour cells in melanoma metastases. Br J Cancer 88, 424-431 (2003).
Oldford, S.A., et al. Tumor cell expression of HLA-DM associates with a Th1 profile and predicts improved survival in breast carcinoma patients. Int Immunol 18, 1591-1602 (2006).
Degenhardt, Y., et al. Distinct MHC gene expression patterns during progression of melanoma. Genes Chromosomes Cancer 49, 144-154 (2010).
Pollack, M.S., Heagney, S.D., Livingston, P.O. & Fogh, J. HLA-A, B, C and DR alloantigen expression on forty-six cultured human tumor cell lines. Journal of the National Cancer Institute 66, 1003-1012 (1981).
Barbieri, G., Rimini, E. & Costa, M.A. Effects of human leukocyte antigen (HLA)-DR engagement on melanoma cells. International journal of oncology 38, 1589-1595 (2011).
Colloby, P.S., West, K.P. & Fletcher, A. Is poor prognosis really related to HLA-DR expression by malignant melanoma cells? Histopathology 20, 411-416 (1992).
Chornoguz, O., Gapeev, A., O'Neill, M.C. & Ostrand-Rosenberg, S. Major histocompatibility complex class II+ invariant chain negative breast cancer cells present unique peptides that activate tumor-specific T cells from breast cancer patients. Mol Cell Proteomics 11, 1457-1467 (2012).
Londei, M., Lamb, J.R., Bottazzo, G.F. & Feldmann, M. Epithelial cells expressing aberrant MHC class II determinants can present antigen to cloned human T cells. Nature 312, 639-641 (1984).
Meazza, R., Comes, A., Orengo, A.M., Ferrini, S. & Accolla, R.S. Tumor rejection by gene transfer of the MHC class II transactivator in murine mammary adenocarcinoma cells. Eur J Immunol 33, 1183-1192 (2003).
Rizvi, N.A., et al. Cancer immunology. Mutational landscape determines sensitivity to PD-1 blockade in non-small cell lung cancer. Science 348, 124-128 (2015).
Wellbrock, C., et al. STAT5 contributes to interferon resistance of melanoma cells. Curr Biol 15, 1629-1639 (2005).
Lee, Y.S., Kim, S.H., Cho, J.A. & Kim, C.W. Introduction of the CIITA gene into tumor cells produces exosomes with enhanced anti-tumor effects. Exp Mol Med 43, 281-290 (2011).
Joseph, R.W., et al. Correlation of NRAS mutations with clinical response to high-dose IL-2 in patients with advanced melanoma. J Immunother 35, 66-72 (2012).
Johnson, D.B., et al. Impact of NRAS Mutations for Patients with Advanced Melanoma Treated with Immune Therapies. Cancer immunology research 3, 288-295 (2015).
Loor, F. & Kindred, B. Differentiation of T-cell precursors in nude mice demonstrated by immunofluorescence of T-cell membrane markers. J Exp Med 138, 1044-1055 (1973).
Rodriguez, T., et al. Patterns of constitutive and IFN-gamma inducible expression of HLA class II molecules in human melanoma cell lines. Immunogenetics 59, 123-133 (2007).
Wolchok, JD., et al. Nivolumab plus Ipilimumab in Advanced Melanoma. The New England journal of medicine (2013).
Postow, M.A., et al. Nivolumab and Ipilimumab versus Ipilimumab in Untreated Melanoma. The New England journal of medicine (2015).
Larkin, J., et al. Combined Nivolumab and Ipilimumab or Monotherapy in Untreated Melanoma. N Engl J Med 373, 23-34 (2015).
Benjamini, Y. & Hochberg, Y. Controlling the False Discovery Rate: A Practical and Powerful Approach to Multiple Testing. Journal of the Royal Statistical Society. Series B (Methodological) 57, 289-300 (1995).
Efron, B. & Tibshirani, R. On testing the significance of sets of genes. Annals of Applied Statistics 1, 107-129 (2007).
Balko, J.M., et al. Profiling of residual breast cancers after neoadjuvant chemotherapy identifies DUSP4 deficiency as a mechanism of drug resistance. Nat Med 18, 1052-1059 (2012).
Balko, J.M., et al. Activation of MAPK pathways due to DUSP4 loss promotes cancer stem cell-like phenotypes in basal-like breast cancer. Cancer Res (2013).
Barretina, J., et al. The Cancer Cell Line Encyclopedia enables predictive modelling of anticancer drug sensitivity. Nature 483, 603-607 (2012).

\* cited by examiner

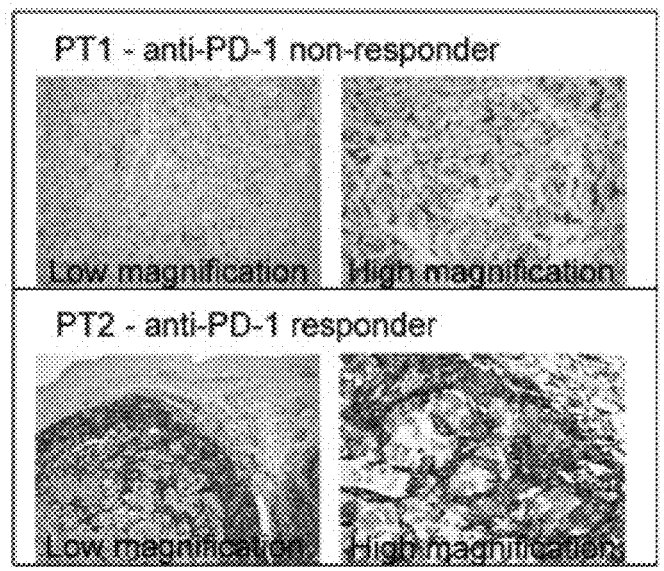
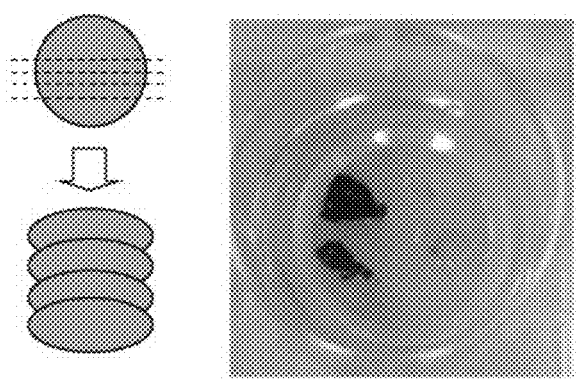
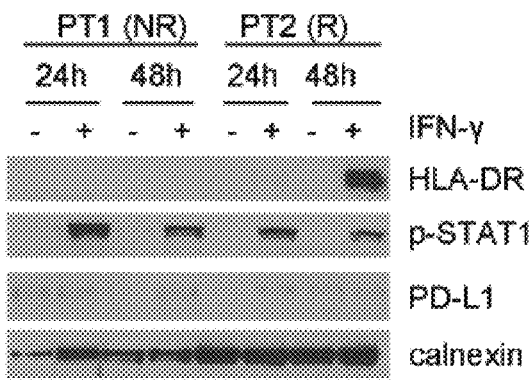
FIG. 6A
FIG. 6B
FIG. 6C
FIG. 6D

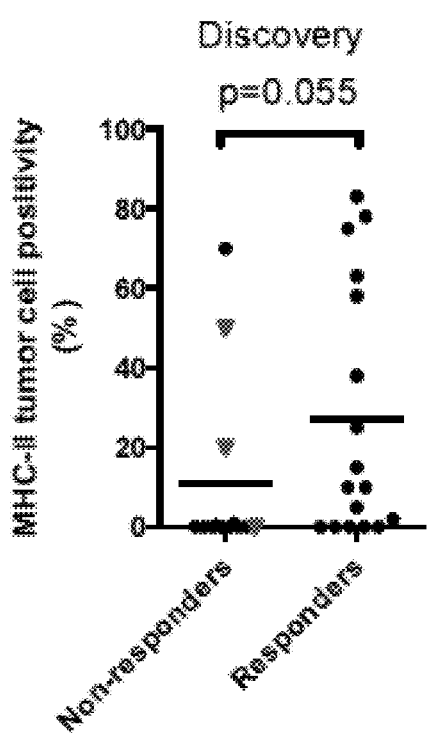
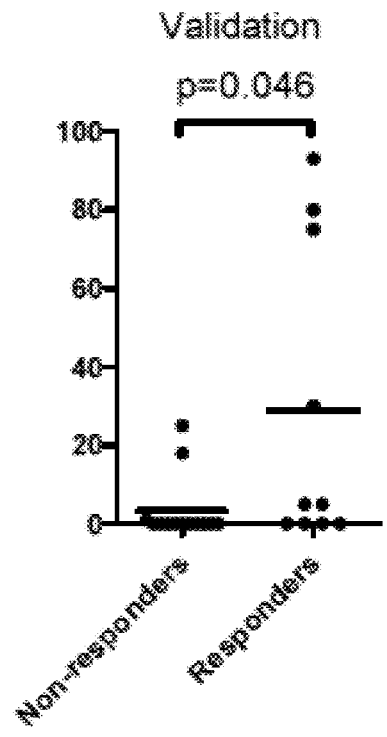
FIG. 7A          FIG. 7B
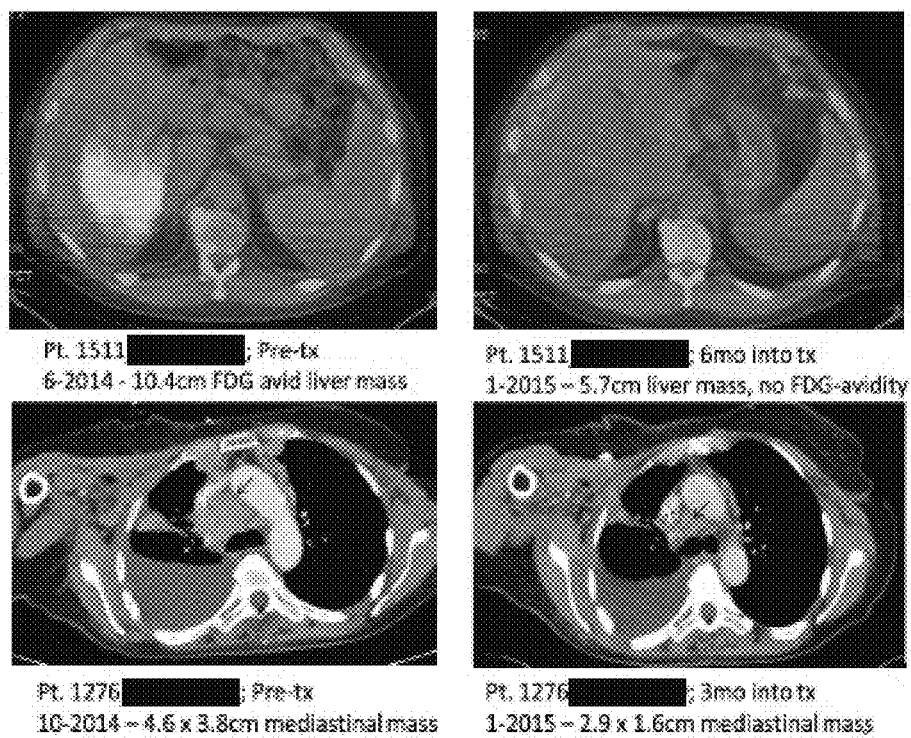
FIG. 7C

METHODS AND SYSTEMS FOR PREDICTING RESPONSE TO IMMUNOTHERAPIES FOR TREATMENT OF CANCER

RELATED APPLICATIONS

This application claims the benefit of U.S. Provisional Application Ser. No. 62/265,714, filed Dec. 10, 2015, the entire disclosure of which is incorporated herein by this reference.

GOVERNMENT INTEREST

This invention was made with government support under P50 CA98131 awarded by the National Institutes of Health. The government has certain rights in the invention.

TECHNICAL FIELD

The presently-disclosed subject matter relates to methods and systems for identifying subjects with cancer likely to benefit from immunotherapy. In particular, the presently-disclosed subject matter relates to determining expression of a major histocompatibility complex-II (MHC-II) molecule in a tumor cell from the subject, predicting whether the subject is likely to benefit from the immunotherapy, and administering the immunotherapy to the subject if the subject is predicted to benefit from the immunotherapy.

BACKGROUND

Immunotherapies that have been approved over the last several years have shown success in treatment of cancer; however, they are costly, they can result in patient toxicity, and they do not benefit all subjects. For example, about 20-50% of melanoma and lung cancers will respond significantly to immunotherapies, while others will not. Thus, identifying which subjects are better candidates for immunotherapy is highly advantageous from a health care and patient quality of life perspective.

PD-L1 is a cell surface glycoprotein that is one of two known ligands for Programmed Death 1 (PD-1). Expression of PD-L1 has been observed on the surface of a variety of immune cells, and PD-L1 mRNA is expressed by non-lymphoid tissues including vascular endothelial cells, epithelial cells, muscle cells, and in tonsil and placental tissue. PD-L1 expression has also been observed in a variety of human cancers, and interaction of tumor-cell expressed PD-L 1 with PD-1 can induce inhibition or apoptosis of tumor-specific T cells. In large sample sets of e.g. ovarian, renal, colorectal, pancreatic, liver cancers and melanoma it has been shown that PD-L1 expression correlated with poor prognosis and reduced overall survival irrespective of subsequent treatment. Anti-PD-1 monoclonal antibodies (mAbs) that block binding of PD-L1 to PD-1 have been shown to have anti-tumor activity against a variety of tumor types, with early human clinical data suggesting that patients whose tumors express PD-L1 are more likely to respond to anti-PD-1 therapy. See International Patent Application Publication No. WO 2014/165422.

Although immunostaining for PD-L1 on tumor cells has been reported to be associated with response in clinical trials, the staining protocol often requires frozen tissue, rather than the formalin-fixed industry standard, and is subject to technical difficulties. Further, the overall accuracy of PD-L1 staining was only 62% in a clinical study (NEJM, PMID:22658127), with imperfect negative and positive predictive value (JCO, PMID:24145345).

Accordingly, there remains a need in the art for a methods and systems for predicting response to immunotherapies, which have improved accuracy for independent use or use in tandem with existing predictive methods, such as PD-L1 staining.

SUMMARY

The presently-disclosed subject matter meets some or all of the above-identified needs, as will become evident to those of ordinary skill in the art after a study of information provided in this document.

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned, likewise, those features can be applied to other embodiments of the presently disclosed subject matter, whether listed in this Summary or not. To avoid excessive repetition, this Summary does not list or suggest all possible combinations of such features.

In some embodiments, a method of detecting cell membrane expression of an MHC molecule in a subject includes (a) obtaining a tumor cell sample from the subject, and (b) detecting cell membrane expression of the MHC molecule by contacting the tumor cell sample with an antibody targeting the MHC molecule and detecting binding between the MHC molecule and the antibody. In some embodiments, the subject is suspected of having cancer and/or being in need of immunotherapy. In on embodiment, the MHC molecule is selected from HLA-A, HLA-B, HLA-C, HLA-DO, HLA-DM, HLA-DR, HLA-DP, HLA-DQ, and HLA-DX. In another embodiment, the MHC molecule is HLA-DR. In a further embodiment, the method includes detecting expression of a marker selected from the group consisting of: HLA-A, HLA-B, HLA-C, PD-1, PD-L1, CD8, CD4, CIITA, Foxp3, LAG3, TIM3, Ox40, Ox40L, 41BB, VISTA, Interferon gamma, Granzyme B, CTLA-4, and SOX-10. In some embodiments, expression of the MHC molecule is measured using at least one method selected from the group consisting of immunohistochemistry, immunofluorescence, flow cytometry, mass-spectroscopy, and combinations thereof.

In one embodiment, the method of detecting cell membrane expression of an MHC molecule in a subject further includes staining for a cancer-specific marker. In another embodiment, the cancer-specific marker is a melanoma-specific marker, such as SOX-10.

In some embodiments, the tumor cell sample is from a cancer selected from: melanoma, lung, ovarian, renal, colorectal, head and neck, bladder, endometrial, pancreatic, breast, and liver cancer. In some embodiments, the tumor cell sample is formalin-fixed. In some embodiments, the tumor cell sample is not a frozen tissue sample.

In some embodiments, a method of treating cancer in a subject with an immunotherapeutic agent includes (a) obtaining a tumor cell sample from the subject, (b) detecting the level of cell membrane expression of the MHC molecule by contacting the tumor cell sample with an antibody targeting the MHC molecule and detecting binding between the MHC molecule and the antibody, and (c) administering a therapeutically effective amount of the immunotherapeutic agent if the level of cell membrane expression of the MHC molecule exceeds a predetermined standard. In one embodiment, the MHC molecule is selected from HLA-A, HLA-B, HLA-C, HLA-DO, HLA-DM, HLA-DR, HLA-DP, HLA-DQ, and HLA-DX. In another embodiment, the MHC molecule is HLA-DR. In a further embodiment, the method further includes detecting expression of a marker selected from the group consisting of: HLA-A, HLA-B, HLA-C, PD-1, PD-L1, CD8, CD4, CIITA, Foxp3, LAG3, TIM3, Ox40, Ox40L, 41BB, VISTA, Interferon gamma, Granzyme B, CTLA-4, and SOX-10. In some embodiments, the tumor cell sample is from a cancer selected from: melanoma, lung, ovarian, renal, colorectal, head and neck, bladder, endometrial, pancreatic, breast, and liver cancer.

In one embodiment, the immunotherapeutic agent is an antibody or an antigen-binding portion thereof that disrupts the interaction between PD-1 and PD-L1. In another embodiment, the immunotherapeutic agent is an antibody selected from anti-CTLA-4, anti-PD-L1, anti-PD-1, anti-LAG3, anti-TIM3, anti-OX40, anti-4-1BB, or an antigen-binding portion thereof.

In some embodiments, the method of treating cancer in a subject further includes administration of a MEK, epigenetic DNA methyltransferase, or histone deacetylase inhibitor.

In some embodiments, the presently-disclosed subject matter includes a complex. In one embodiment, the complex includes a tumor cell having a cell surface-expressed MHC molecule in complex with an antibody or an antigen-binding portion thereof that binds specifically to the MHC molecule.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 6A-D show Ex vivo culture of tumours derived from anti-PD-1-responding and non-responding patients identifies heterogeneity in interferon response. (A) Patient tumour blocks stained for HLA-DR (brown) and SOX10 (pink) at low (scale bar, 500 um) and high magnification (scale bar, 200 gm); PT1: anti-PD-1 non-responder and PT2: anti-PD-1 responder. (B) Experimental schema. (C) Schema and images of PDX tissue sections (ex vivo organotypic culture). (D) Western blot analysis of tissue sections cultured in the presence or absence of IFNy for 24-48 h.

FIGS. 7A-E show MHC-II(+) melanomas have improved response rates and clinical benefit to PD-1/PD-1.1 inhibition. (A) HLA-DR positivity by IHC plotted versus response to PD-1/PD-L1-targeted therapy in the discovery set (n=30). Responders include partial and complete responders; non-responders include mixed responders and progressive disease patients. Mixed responders (n=3) are noted by a red triangle. P value is the result of the Wilcoxon's rank sum test. (B) HLA-DR positivity by IHC in the validation set (n=23) plotted versus response to PD-1/PD-L1-targeted therapy. P value is the result of the Wilcoxon's rank sum test (C) Representative images of scans from anti-PD-1 therapy-treated MHC-II(+) patients (D) Progression-free survival (left) and overall survival (right) in anti-PD-1PD-L1-treated patients, stratified by HLA-DR/MHC-II positivity (5% total tumour cells staining on entire tissue section used as cut-point). Data from both the initial and validation cohorts were included, when available. P value is the result of the log-rank test. (E) Correlation matrix of IHC markers. P values for the Pearson's correlation appear above the diagonal and correlation coefficients (r) appear below the diagonal.

DETAILED DESCRIPTION

Figure 1A:
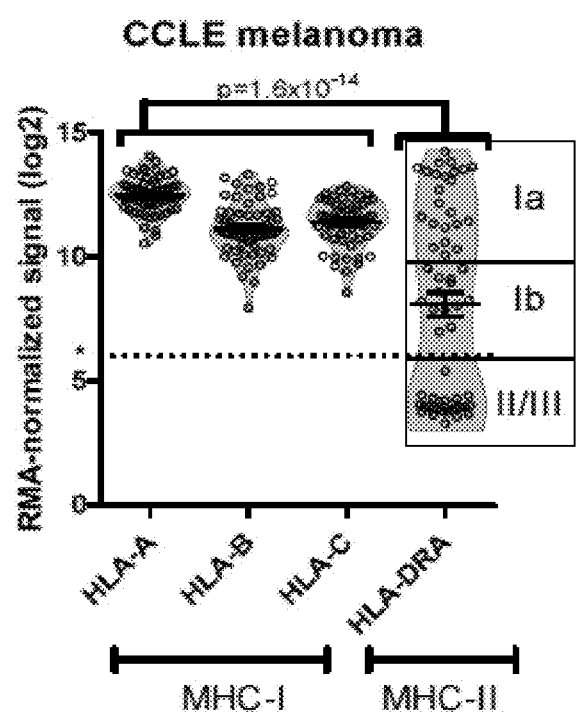
FIGS. 1A-C A unique subtype of melanoma expresses MHC-II. (A) Microarray data from 60 melanoma cell lines in the CCLE48 were analysed for MHC-I (HLA-A/B/C) and MHC-II (HLA-DRA) expression. Bars represent the mean±S.D. P-value is the result of the Kolmogorov-Smirnov test comparing the distribution of MHC-I (HLA-A, HLA-B, HLA-C) expression with MHC-II expression (HLA-DRA). *represents the cutoff for defining MHC-II(+). (B) Gene-expression data from HLA-DRA(+) cell lines (Clusters 1a/1b) were compared with HLA-DRA(−) cell lines (Clusters II and III) by an FDR-corrected row t-test. Significantly altered genes are shown on the y-axis and also listed in Supplementary Data 1 (Table 1). An ad hoc heat map is shown at the top, highlighting classical MHC-II genes. (C) Normalized microarray data were analysed by GSA47 using the curated Molecular Signatures Database, and the resulting gene set scores are presented as a hierarchical clustered heat map.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent.

In some embodiments a subject will be administered an effective amount of at least one compound and/or composition provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products.

Additionally, the terms "subject" or "subject in need thereof" refer to a target of administration, which optionally displays symptoms related to a cancer. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

As will be recognized by one of ordinary skill in the art, the terms "suppression," "suppressing," "suppressor," "inhibition," "inhibiting" or "inhibitor" do not refer to a complete elimination of angiogenesis in all cases. Rather, the skilled artisan will understand that the term "suppressing" or "inhibiting" refers to a reduction or decrease in angiogenesis. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

As used herein, the terms "treatment" or "treating" relate to any treatment of a cancer. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

The presently-disclosed subject matter includes a method of predicting whether a subject is likely to benefit from treatment with an immunotherapy, and a method of treating a subject having cancer. Also disclosed are kits useful for treating and/or predicting whether a subject is likely to benefit from treatment with an immunotherapy.

In some embodiments, the method of predicting whether a subject is likely to benefit from treatment with an immunotherapy includes detecting cell membrane expression of an MHC molecule in the subject. In one embodiment, the method involves providing a tumor cell sample from the subject, and determining the level of cell membrane expression of a major histocompatibility complex (MHC) molecule. In another embodiment, the method also includes identifying the subject as likely to benefit from treatment with the immunotherapeutic agent based if the level of cell membrane expression of the MHC molecule exceeds a predetermined standard. In a further embodiment, the MHC molecule is selected from an MHC-I or MHC-II molecule, in the tumor cell sample. In some embodiments, the subject is suspected of having cancer and/or being in need of cancer treatment, such as immunotherapy. The method can be performed ex vivo or in vitro.

In some embodiments, the method of treating a subject having cancer with an immunotherapeutic agent involves identifying a subject likely to benefit from treatment with the immunotherapeutic agent, and administering a therapeutically effective amount of the immunotherapeutic agent. The step of identifying the subject likely to benefit involves providing a tumor cell sample from the subject; determining the level of cell membrane expression of a MHC molecule, selected from an MHC-I or MHC-II molecule, in the tumor cell sample; and identifying the subject as likely to benefit from treatment with the immunotherapeutic agent based if the level of cell membrane expression of the MHC molecule exceeds a predetermined standard.

A "predetermined standard" or "reference" can include, for example, a level cell membrane expression of the MHC molecule in one or more tumor cell samples from one or more individuals having a particular cancer of interest. In some embodiments, the reference can include control data. Control data, when used as a reference, can comprise compilations of data, such as may be contained in a table, chart, graph, e.g., standard curve, or database, which provides amounts or levels of cell membrane expression of the MHC molecule considered to be threshold levels or control levels. Such data can be compiled, for example, by obtaining expression levels from one or more tumor cell samples (e.g., an average of amounts or levels from multiple samples) from one or more individuals with the cancer of interest or without the cancer of interest.

In connection with the methods disclosed herein, the level of cell membrane expression of a MHC molecule, or marker, is determined. The MHC molecule is selected from an MHC-I or MHC-II molecule. In some embodiments, the MHC molecule is selected from HLA-A, HLA-B, HLA-C, HLA-DO, HLA-DM, HLA-DR, HLA-DP, HLA-DQ, and HLA-DX. In some embodiments, multiple distinct MHC molecules, or markers, are detected. For example, in one embodiment, the MHC molecule includes HLA-DR. In another embodiment, the MHC molecule includes HLA-DR and at least one of HLA-A, HLA-B, HLA-C, PD-1, or PD-L1. Additionally or alternatively, the markers may include, but are not limited to, CD8, CD4, CIITA, Foxp3, LAG3, TIM3, Ox40, Ox40L, 41BB, VISTA, Interferon gamma, Granzyme B, interferon gamma response gene signatures, CTLA-4, SOX-10, or a combination thereof. As will be recognized by one of ordinary skill in the art about study of the present application, the expression of the MHC molecule can be measured using a variety of methods, for example, immunohistochemistry, immunofluorescence, flow cytometry, and/or mass-spectroscopy methods.

In some embodiments of the methods disclosed herein, it can be beneficial to also probe for a cancer-specific marker, e.g., a dual stain, to facilitate identification of cancer cells in the sample. For one non-limiting example, the cancer-specific marker could be a melanoma-specific marker, such as SOX-10.

The term "cancer" refers to all types of cancer or neoplasm or malignant tumors found in animals, including leukemias, carcinomas, melanoma, and sarcomas. Examples of cancers include, but are not limited to, melanoma, lung, ovarian, renal, colorectal, head and/or neck, bladder, endometrial, pancreatic, breast, and/or liver cancer.

The presently-disclosed subject matter has the benefit of being useful in connection with a variety of tissue preparations. For example, while the methods disclosed herein can be used in connection with frozen tissue, frozen tissue is not required. Indeed, the methods can be used in connection with a formalin-fixed sample.

In some embodiments of the presently-disclosed subject matter, a subject identified as being likely to benefit from treatment is administered such treatment. In this regard, some embodiments of the methods further include administration of an immunotherapeutic agent. In some embodiments, the immunotherapeutic agent is an antibody or an antigen-binding portion thereof that disrupts the interaction between PD-1 and PD-L1. In some embodiments, the immunotherapeutic agent is an antibody selected from anti-CTLA-4, anti-PD-L1, anti-PD-1, anti-LAG3, anti-TIM3, anti-Ox40, anti-4-IBB, or an antigen-binding portion thereof. In some embodiments, the method optionally involves administering a MEK, epigenetic DNA methyltransferase, and/or histone deacetylase inhibitor. Examples of MEK inhibitors include, but are not limited to, Selumetinib (AstraZeneca), PD0325901 (Pfizer), Pimasertib, MEK inhibitor AS703026 (Merck Serono), Cobimetinib (Exelixis), Trametinib (Mekinist), binimetinib (Array BioPharma Inc), MEK inhibitor WX-554 (Wilex), refametinib (Ardea Biosciences), and AZD8330 (AstraZeneca).

The presently-disclosed subject matter further includes kits useful for treating and/or predicting whether a subject is likely to benefit from treatment with an immunotherapy. In some embodiments, the kit includes a probe for a MHC molecule, selected from an MHC-I or MHC-II molecule. The kit can optionally include standards to which the level of cell membrane expression of the MHC molecule in the tissue sample from the subject is compared. In some embodiments, wherein the MHC molecule is selected from one or more of HLA-A, HLA-B, HLA-C, HLA-DA, HLA-DM, HLA-DR, HLA-DP, HLA-DQ, and HLA-DX.

The probe included in the kit can be, for example, an antibody or an antigen-binding portion thereof that binds specifically to the cell surface-expressed MHC molecule. In some embodiments, the antibody or an antigen-binding portion thereof binds specifically to the cell surface-expressed MHC molecule in a formalin-fixed, paraffin-embedded (FFPE) tissue sample. The antibody or an antigen-binding portion can optionally include a tag, such as a fluorescent tag. In some embodiments, the kit includes a secondary antibody including a tag.

In some embodiments, the kit can optionally include a cancer-specific marker. For example, the cancer-specific marker could be a melanoma-specific marker, such as SOX-10.

In some embodiments of the kit, an immunotherapeutic agent is also provided. For example, the immunotherapeutic agent can be an antibody or an antigen-binding portion thereof that disrupts the interaction between PD-1 and PD-L1. In some embodiments, the immunotherapeutic agent is an antibody selected from anti-CTLA-4, anti-PD-L1, anti-PD-1, anti-LAG3, anti-TIM3, anti-Ox40, anti-4-1BB, or an antigen-binding portion thereof.

In some embodiments of the kit, a MEK, epigenetic DNA methyltransferase, and/or histone deacetylase inhibitor is also provided. Examples of MEK inhibitors include, but are not limited to, Selumetinib (AstraZeneca), PD0325901 (Pfizer), Pimasertib, MEK inhibitor AS703026 (Merck Serono), Cobimetinib (Exelixis), Trametinib (Mekinist), binimetinib (Array BioPharma Inc), MEK inhibitor WX-554 (Wilex), refametinib (Ardea Biosciences), and AZD8330 (AstraZeneca).

The presently-disclosed subject matter further includes a cell surface-expressed MHC molecule, as disclosed herein, in complex with an antibody or an antigen-binding portion thereof that binds specifically to the MHC molecule, as disclosed herein.

The presently-disclosed subject matter is further illustrated by the following specific but non-limiting examples. The following examples may include compilations of data that are representative of data gathered at various times during the course of development and experimentation related to the present invention.

EXAMPLES

Example 1: Melanoma-Specific MHC-II Expression Represents a Tumor-Autonomous Phenotype and Predicts Response to Anti-PD-1/PD-L1 Therapy Abstract Anti-PD-1 therapy yields objective clinical responses in 30-40% of advanced melanoma patients. Since most patients do not respond, predictive biomarkers to guide treatment selection are needed. In view thereof, this example examines whether MHC-I/II expression is required for tumor antigen presentation and may predict response to anti-PD-1 therapy. Across 60 melanoma cell lines, bimodal expression patterns of MHC-II were found, while MHC-I expression was ubiquitous. A unique subset of melanomas are capable of expressing MHC-II under basal or IFNγ stimulated conditions. Using pathway analysis, it was found that MHC-II(+) cell lines demonstrate signatures of 'PD-1 signaling', 'allograft rejection', and 'T-cell receptor signaling', among others. In two independent cohorts of anti-PD-1-treated melanoma patients, MHC-II positivity on tumor cells was strongly associated with response to therapy, progression-free survival, and overall survival. MHC-II positivity also correlated with CD4+ and CD8+ tumor infiltrate. Accordingly, it was concluded that some melanomas demonstrate an autonomous MHC-II signature that correlates with anti-PD-1 response and enhanced T-cell infiltrate. MHC-II+ tumors can be robustly identified by routine melanoma-specific immunohistochemistry using commercially available antibodies for HLA-DR to improve anti-PD-1 patient selection.

Introduction

Monoclonal antibodies blocking the programmed death-1 (PD-1) receptor or its ligand (PD-L1) relieve the suppression of anti-tumor immune responses in a variety of cancers. Durable remissions occur in sizable fractions of patients with melanoma (30-40%), non-small cell lung cancer (15-20%), renal cell carcinoma (20-30%), bladder urothelial carcinoma (30%), Hodgkin lymphoma (80-90%), and others including head and neck squamous cell carcinoma and triple negative breast cancer. Accurate predictive markers of therapeutic efficacy are needed to optimize patient selection, improve treatment decision-making, and minimize costs. To date, several candidate approaches have been identified in melanoma. These include tumor or immune cell expression of PD-L1, identification of neo-antigens through next generation sequencing techniques, and T-cell receptor clonality profiling. While quite promising, these assays are technically challenging and require specialized tissue processing.

Tumors evade immune surveillance by immune checkpoint expression (PD-L1 and others), immunosuppressive cytokine profiles, tolerogenic immune cell recruitment (regulatory T-cells and others), and cancer-specific cell signaling. In addition, cancer cells can lose the ability to present tumor antigens, thus avoiding recognition by cytotoxic T cells and antigen presenting cells. Down-regulation of major histocompatibility class I and II (MHC-I and MHC-II) has been linked to immune suppression, metastatic progression, and a poor prognosis in numerous malignancies.

Despite the established importance of tumor-specific antigen expression, the influence of MHC-I and MHC-II expression on response to new immune therapies, particularly anti-PD-1/PD-L1, has not been explored. Specifically, HLA-DR is frequently expressed on melanoma and has unclear functional and prognostic significance. Without wishing to be bound by theory, it is believed that MHC-I and MHC-II expression, particularly HLA-DR, are required for anti-PD-1/PD-L1 activity and serve as technically and clinically feasible predictive biomarkers for therapeutic efficacy. As shown in this example, melanoma-specific expression of HLA-DR marks tumours with unique inflammatory signals that are more responsive to PD-1 targeted therapy. Accordingly, it is believed that tumor-specific HLA-DR expression may be used as a biomarker of high likelihood of response to these agents.

Results

Antigen presenting MHC-I and MHC-II pathways in melanoma cell lines. Based on the known biological interactions of PD-1/PD-L1 signaling, antigen presentation by tumor or professional antigen-presenting cells is hypothesized to be a requirement for immune recognition of the malignant cell. MHC-I presents antigen to CD8+ cytotoxic T lymphocytes (CTL) and is ubiquitously expressed by most cells. Loss of MHC-I is typically thought to trigger natural-killer (NK) cell checkpoints, resulting in NK-mediated cytotoxicity. In contrast, MHC-II, which presents antigen to CD4+ T helper cells, is typically restricted to professional antigen-presenting cells (APCs) such as dendritic cells and B cells. HLA-DR, the primary antigen-presenting molecule of the MHC-II pathway is expressed in some cancers, particularly in response to CTL-secreted interferon-gamma (IFNγ). Some data suggest that non-immune cells, including cancer cells can function as MHC-II+ APCs. Given the heterogeneity of the tumor milieu, a question arose as to whether MHC-I and II were expressed in in vitro cell line models of melanoma (rather than in resected melanoma tumors), where the contribution of stromal and infiltrating immune cells could be excluded.

Figure 1B:
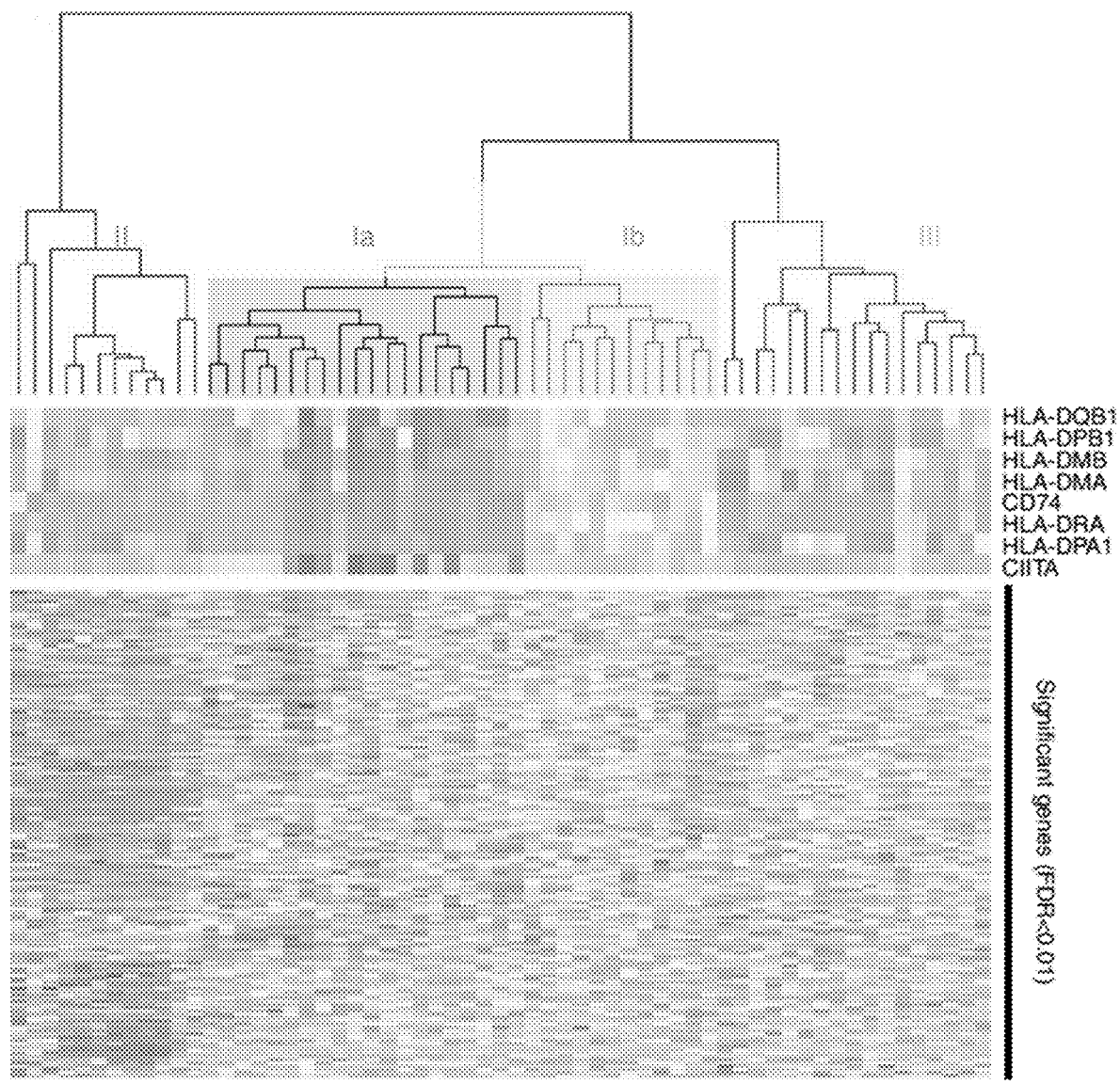
Figure 1C:
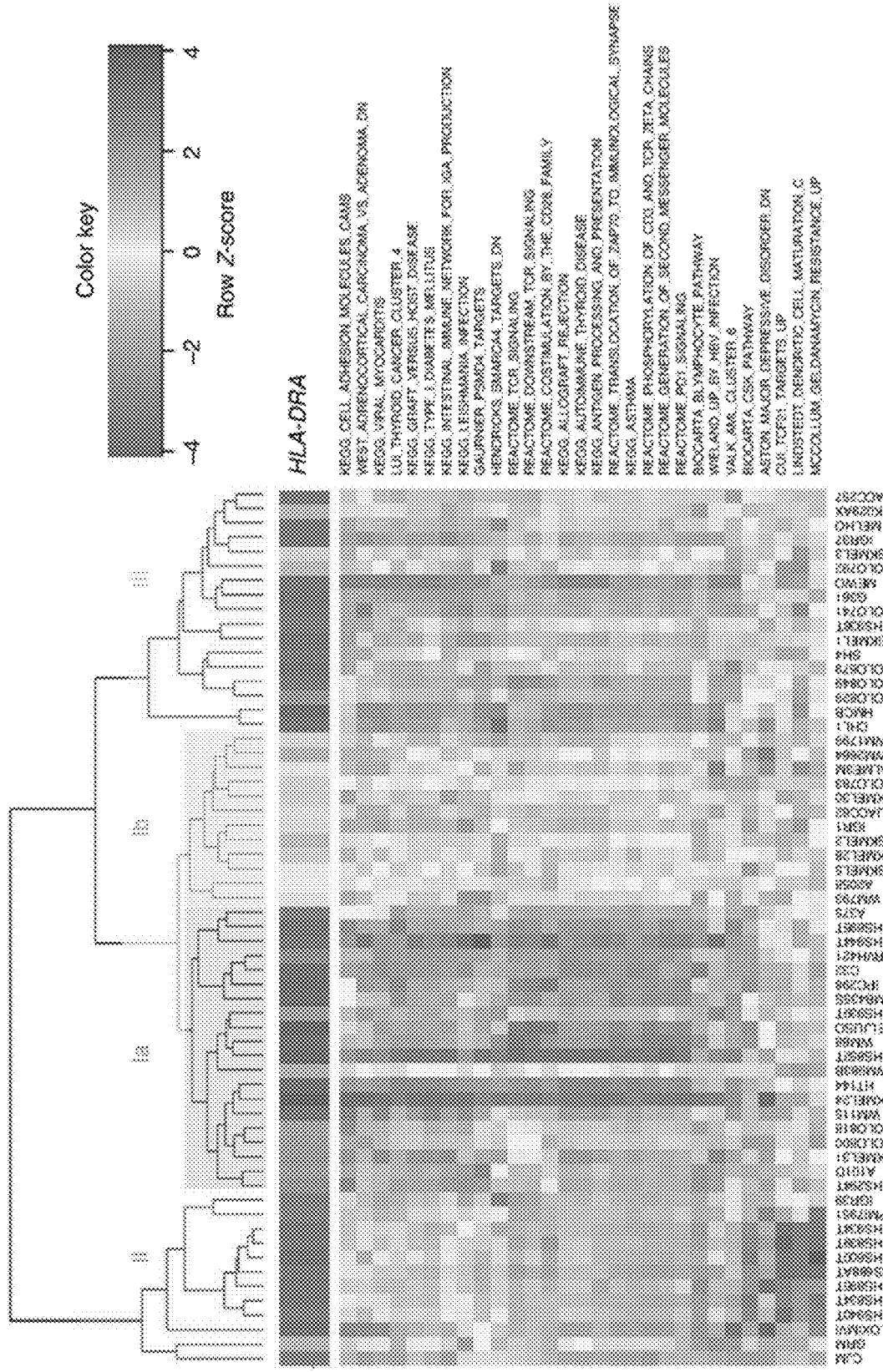
Figure 2:
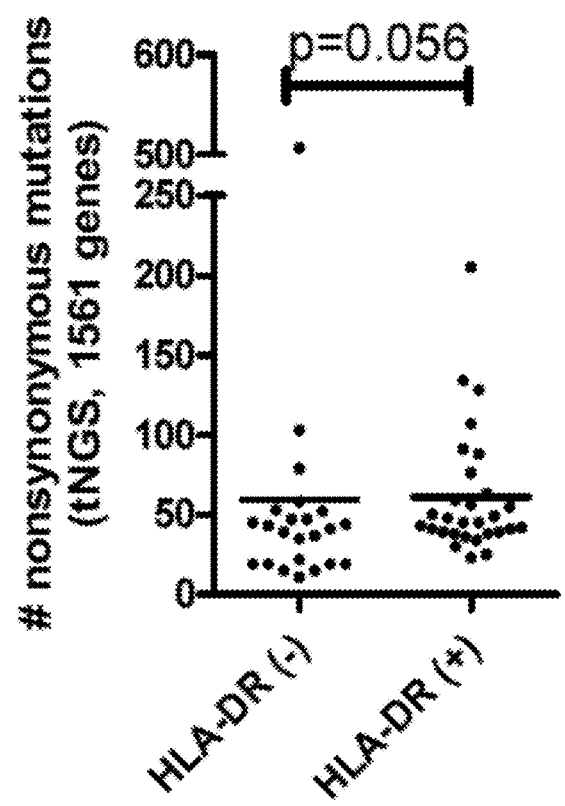
FIG. 2 shows a graph illustrating that HLA-DR(+) melanoma cell lines are associated with a higher mutational burden. CCLE melanoma cell lines (n=61) plotted against total expressed mutational burden. Number of non-synonymous mutations was determined by targeted sequencing of 1561 genes and these data and associated information are available in the CCLE project through cBio portal (cbioportal.org).

Using the Cancer Cell Line Encyclopedia (CCLE) melanoma panel of 60 cell lines, it was determined that MHC-I mRNA expression (using HLA-A as the prototype) was ubiquitously high across almost all melanoma cell lines (FIG. 1A). In contrast, HLA-DRA, the prototype MHC-II molecule, demonstrated a strong bimodal distribution pattern, and appeared absent in approximately 50% of cell lines (FIG. 1A). The remaining cell lines demonstrated intermediate to high mRNA levels. When cell lines were factored according to HLA-DRA mRNA (using an arbitrary cutoff of 6 (RMA log 2 signal intensity), there was a signature of 159 genes (Table 1) which were significantly altered (up or downregulated, FDR<1%) in HLA-DRA-expressing cells compared to those cell lines lacking HLA-DRA mRNA (FIG. 1B). Clustering on these genes suggested 4 clusters of expression patterns, which were identified as clusters Ia and Ib (predominantly HLA-DR-expressing) and clusters II and III (predominantly HLA-DR-negative). Gene set analysis (GSA) of the CCLE based on MHC-II classification yielded 27 gene sets with upregulated scores and 1 with a downregulated score at an FDR<5% in the Ia/Ib subtype. Bioinformatics analysis of the enriched gene sets suggested that HLA-DRA-expressing cell lines harbored expression signatures of 'PD-1 signaling', 'T-cell receptor signaling', 'graft-versus-host disease', and 'allograft rejection' (FIG. 1C). These findings suggested that there were tumor-cell autonomous signaling pathways driving MHC-II expression consistent with a pro-immune/anti-tumor response. The presence of a high mutational burden and resulting neoantigens has been shown to predict response to PD-L1 therapy in lung cancer. HLA-DR-expressing melanoma lines had a higher total nonsynonymous mutational load by targeted next-generation sequencing of 1,561 genes, although this was not statistically significant (Wilcoxon Rank Sum p=0.056, FIG. 2).

TABLE 1

Genes altered in MHC-II (+) melanoma cell lines versus MHC-II (−) cell lines

| Gene ID | T-statistic | Log2 Fold Change HLA-DR+ versus HLA-DR− | P-value (uncorrected) | False Discovery Rate |
| --- | --- | --- | --- | --- |
| HLA-DRA | 15.213927 | 6.8995504 | 4.38E-22 | 8.80E-18 |
| CD74 | 10.845865 | 5.4611784 | 1.12E-15 | 1.13E-11 |
| HLA-DPA1 | 9.851692 | 5.0791636 | 4.49E-14 | 3.01E-10 |
| S100B | 5.592843 | 4.2563749 | 6.06E-07 | 3.58E-04 |
| PLP1 | 4.849015 | 3.5828047 | 9.41E-06 | 2.56E-03 |
| HLA-DMA | 8.661834 | 3.5538701 | 4.20E-12 | 2.11E-08 |
| SNX10 | 5.406524 | 3.3458826 | 1.22E-06 | 6.28E-04 |
| FABP7 | 5.594157 | 3.3277273 | 6.03E-07 | 3.58E-04 |
| NFATC2 | 6.060418 | 3.3201765 | 1.03E-07 | 9.83E-05 |
| PTPRZ1 | 5.176045 | 3.0896493 | 2.86E-06 | 1.01E-03 |
| NGFR | 5.925755 | 3.0076695 | 1.72E-07 | 1.50E-04 |
| FLRT3 | 6.584844 | 2.9601229 | 1.36E-06 | 2.73E-05 |
| MMP8 | 4.697741 | 2.9277593 | 1.62E-05 | 3.70E-03 |
| TGFA | 4.705974 | 2.800589 | 1.57E-05 | 3.70E-03 |
| GAS7 | 6.389378 | 2.7747686 | 2.90E-08 | 3.64E-05 |
| ERBB3 | 4.824419 | 2.7459398 | 1.03E-05 | 2.69E-03 |
| ROPN1 | 5.313675 | 2.7099096 | 1.72E-07 | 7.56E-04 |
| MIA | 5.198919 | 2.6799177 | 2.63E-06 | 9.79E-04 |
| HLA-DPB1 | 5.293034 | 2.6171656 | 1.86E-06 | 7.94E-04 |
| ASB9 | 6.514841 | 2.5990046 | 1.78E-08 | 2.99E-05 |
| SHROOM2 | 6.779445 | 2.592674 | 6.38E-09 | 1.83E-05 |
| TRIM9 | 6.482923 | 2.5090333 | 2.02E-08 | 3.05E-05 |
| LYPD1 | 6.106807 | 2.4834576 | 8.59E-08 | 8.64E-05 |
| SYNM | 6.469599 | 2.4805447 | 2.12E-08 | 3.05E-05 |
| EPHA3 | 4.355389 | 2.4732033 | 5.37E-05 | 7.61E-03 |
| SLC35F1 | 6.166944 | 2.4706035 | 6.82E-08 | 7.22E-05 |
| HLA-DQB1 | 4.789133 | 2.4531794 | 1.17E-05 | 2.97E-03 |
| SORBS2 | 4.834557 | 2.4447783 | 9.91E-06 | 2.66E-03 |
| GNG2 | 6.685527 | 2.4378914 | 9.20E-09 | 2.31E-05 |
| UGT8 | 4.829512 | 2.3379229 | 1.01E-05 | 2.67E-03 |
| ITGB3 | 5.082412 | 2.2978034 | 4.03E-06 | 1.29E-03 |
| SLITRK6 | 4.386808 | 2.2690057 | 4.82E-05 | 7.02E-03 |
| ITGB8 | 5.056133 | 2.2372412 | 4.44E-06 | 1.39E-03 |
| TRPM8 | 4.466726 | 2.2089335 | 3.65E-05 | 5.77E-03 |
| HLA-DMB | 7.729596 | 2.2029647 | 1.57E-10 | 6.31E-07 |
| TMTC2 | 6.011463 | 2.1882044 | 1.24E-07 | 1.13E-04 |
| SHC4 | 5.106523 | 2.1758035 | 3.70E-06 | 1.21E-03 |
| POU3F2 | 5.709246 | 2.0811539 | 3.91E-07 | 2.64E-04 |
| TFAP2C | 4.29478 | 2.0657408 | 6.62E-05 | 8.58E-03 |
| SYTL2 | 5.319357 | 2.0496798 | 1.68E-06 | 7.56E-04 |
| TNFRSF21 | 5.547299 | 2.0424787 | 7.19E-07 | 4.02E-04 |
| AGPAT9 | 5.262261 | 2.0308708 | 2.08E-06 | 8.60E-04 |
| FAM78B | 4.641567 | 2.0234908 | 1.97E-05 | 3.96E-03 |
| ST6GAL1 | 4.444329 | 2.0159904 | 3.95E-05 | 5.92E-03 |
| TM4SF18 | 4.526559 | 2.0130853 | 2.96E-05 | 5.19E-03 |
| HIVEP3 | 5.186298 | 1.9981964 | 2.75E-06 | 9.89E-04 |
| CLMN | 6.559112 | 1.9552922 | 1.50E-08 | 2.75E-05 |
| TIAM1 | 5.666435 | 1.9343871 | 4.59E-07 | 2.89E-04 |
| SIPA1L2 | 5.103054 | 1.9284935 | 3.74E-06 | 1.21E-03 |
| FHDC1 | 7.649529 | 1.9267439 | 2.15E-10 | 7.19E-07 |
| FREM2 | 4.675119 | 1.8894848 | 1.75E-05 | 3.74E-03 |
| SLC26A2 | 6.429413 | 1.8663853 | 2.48E-08 | 3.33E-05 |
| RASSF4 | 4.881541 | 1.8639941 | 8.37E-06 | 2.35E-03 |
| SPATA13 | 5.896206 | 1.8077273 | 1.92E-07 | 1.61E-04 |

TABLE 1-continued

Genes altered in MHC-II (+) melanoma cell lines versus MHC-II (−) cell lines

| Gene ID | T-statistic | Log2 Fold Change HLA-DR+ versus HLA-DR− | P-value (uncorrected) | False Discovery Rate |
| --- | --- | --- | --- | --- |
| FRMD5 | 5.455314 | 1.7843982 | 1.02E-06 | 5.37E-04 |
| RNF125 | 4.273905 | 1.7842557 | 7.11E-05 | 9.06E-03 |
| B4GALT6 | 5.73706 | 1.7646051 | 3.52E-07 | 2.53E-04 |
| ATP10B | 4.362509 | 1.7340418 | 5.24E-05 | 7.51E-03 |
| TMEM171 | 4.636609 | 1.7333361 | 2.01E-05 | 3.96E-03 |
| RTP4 | 4.697952 | 1.6884598 | 1.62E-05 | 3.70E-03 |
| KAT2B | 5.378765 | 1.685032 | 1.35E-06 | 6.68E-04 |
| FOXD3 | 4.424441 | 1.6731433 | 4.23E-05 | 6.21E-03 |
| CSRP2 | 4.315628 | 1.6639551 | 6.16E-05 | 8.21E-03 |
| CHST6 | 5.137389 | 1.6217742 | 3.30E-06 | 1.12E-03 |
| LPCAT2 | 5.707336 | 1.5952037 | 3.93E-07 | 2.64E-04 |
| PREX1 | 4.511328 | 1.5765817 | 3.12E-05 | 5.24E-03 |
| TNC | 4.670963 | 1.5484352 | 1.78E-05 | 3.74E-03 |
| CIITA | 5.169709 | 1.5433302 | 2.93E-06 | 1.02E-03 |
| MARCKSL1 | 5.376473 | 1.5427519 | 1.36E-06 | 6.68E-04 |
| INPP5F | 4.62986 | 1.5315523 | 2.06E-05 | 4.02E-03 |
| SAMD5 | 4.553002 | 1.4635345 | 2.70E-05 | 4.89E-03 |
| PLXNB3 | 5.209431 | 1.4616735 | 2.53E-06 | 9.79E-04 |
| MAML3 | 4.461074 | 1.459821 | 3.72E-05 | 5.79E-03 |
| GLDC | 4.334158 | 1.4477283 | 5.78E-05 | 7.91E-03 |
| ST3GAL4 | 4.66421 | 1.433675 | 1.82E-05 | 3.76E-03 |
| KHDRBS3 | 4.722392 | 1.427277 | 1.48E-05 | 3.59E-03 |
| LDLRAD4 | 4.561478 | 1.427108 | 2.62E-05 | 4.79E-03 |
| ITGA6 | 5.199928 | 1.4205761 | 2.62E-06 | 9.79E-04 |
| PMP22 | 5.321876 | 1.4010431 | 1.67E-06 | 7.56E-04 |
| BFSP1 | 5.048322 | 1.3644542 | 4.57E-06 | 1.39E-03 |
| EXTL1 | 5.504541 | 1.3540492 | 8.44E-07 | 4.59E-04 |
| GULP1 | 4.361196 | 1.3323331 | 5.26E-05 | 7.51E-03 |
| ACP6 | 5.048185 | 1.3318244 | 4.57E-06 | 1.39E-03 |
| TNS3 | 5.235553 | 1.3236621 | 2.30E-06 | 9.24E-04 |
| SDC3 | 4.734534 | 1.3226811 | 1.42E-05 | 3.48E-03 |
| ZNF827 | 4.780905 | 1.2975313 | 1.20E-05 | 2.98E-03 |
| SPATA6 | 5.187201 | 1.2373858 | 2.75E-06 | 9.89E-04 |
| PAQR8 | 4.625539 | 1.1707259 | 2.09E-05 | 4.04E-03 |
| CUBN | 4.525968 | 1.1344845 | 2.97E-05 | 5.19E-03 |
| DAG1 | 6.205058 | 1.1210876 | 5.89E-08 | 6.58E-05 |
| ABCB9 | 6.603694 | 1.1156536 | 1.26E-08 | 2.73E-05 |
| SNRPB2 | 4.672014 | 1.0888635 | 1.77E-05 | 3.74E-03 |
| LINC00327 | 4.956843 | 1.0438048 | 6.37E-06 | 1.88E-03 |
| PYGB | 4.662699 | 1.0210988 | 1.83E-06 | 3.76E-03 |
| HOXC13 | 4.304304 | 1.0195866 | 6.40E-05 | 8.47E-03 |
| TMX4 | 4.322439 | 0.9882031 | 6.02E-05 | 8.12E-03 |
| DPY19L1 | 4.454231 | 0.9013517 | 3.81E-05 | 5.85E-03 |
| SPRY2 | 4.6715 | 0.8697505 | 1.78E-05 | 3.74E-03 |
| HP55 | 5.203752 | 0.8356998 | 2.58E-06 | 9.79E-04 |
| SRGAP2 | 4.924721 | 0.8285677 | 7.16E-06 | 2.06E-03 |
| CDK5 | 4.58497 | 0.8165132 | 2.41E-05 | 4.52E-03 |
| IFNGR2 | 5.825123 | 0.7982793 | 2.52E-07 | 1.95E-04 |
| DCPS | 4.378902 | 0.7639304 | 4.95E-05 | 7.16E-03 |
| SHROOM4 | 4.94164 | 0.7509587 | 6.73E-06 | 1.96E-03 |
| PIAS2 | 4.348352 | 0.7476783 | 5.50E-05 | 7.74E-03 |
| ITPK1 | 4.636603 | 0.7457709 | 2.01E-05 | 3.96E-03 |
| CD58 | 4.517366 | 0.7443327 | 3.06E-05 | 5.24E-03 |
| ADCK3 | 4.315287 | 0.7371069 | 6.17E-05 | 8.21E-03 |
| VPS37B | 5.796215 | 0.7347872 | 2.81E-07 | 2.09E-04 |
| ABTB2 | 4.451921 | 0.7210315 | 3.84E-05 | 5.86E-03 |
| RFX5 | 4.47776 | 0.6708229 | 3.51E-05 | 5.69E-03 |
| PITPNM2 | 4.694316 | 0.6704875 | 1.64E-05 | 3.70E-03 |
| CTSE | 4.543744 | 0.6652288 | 2.79E-05 | 4.99E-03 |
| CCSAP | 4.4481 | 0.6474003 | 3.90E-05 | 5.89E-03 |
| NFKB1 | 4.999332 | 0.635211 | 5.46E-06 | 1.64E-03 |
| ABCF2 | 4.617906 | 0.622915 | 2.15E-05 | 4.11E-03 |
| ZCCHC17 | 4.701173 | 0.5407589 | 1.60E-05 | 3.70E-03 |
| GUCD1 | 4.338599 | 0.5142809 | 5.69E-05 | 7.89E-03 |
| NUBP1 | 4.325669 | 0.4947412 | 5.95E-05 | 8.08E-03 |
| ZC3H4 | 4.612174 | 0.4700155 | 2.19E-05 | 4.16E-03 |
| ZMIZ2 | 4.563336 | 0.4554563 | 2.60E-05 | 4.79E-03 |
| LOC729870 | 4.466489 | 0.4304289 | 3.65E-05 | 5.77E-03 |
| BTBD16 | 4.298153 | 0.1890444 | 6.54E-05 | 8.54E-03 |
| MSR1 | −4.426413 | −0.3551014 | 4.20E-05 | 6.21E-03 |
| LOC100130417 | −4.707529 | −0.3555586 | 1.56E-05 | 3.70E-03 |
| SMARCAL1 | −4.334969 | −0.381422 | 5.76E-05 | 7.91E-03 |

TABLE 1-continued

Genes altered in MHC-II (+) melanoma cell lines versus MHC-II (−) cell lines

| Gene ID | T-statistic | Log2 Fold Change HLA-DR+ versus HLA-DR− | P-value (uncorrected) | False Discovery Rate |
|---|---|---|---|---|
| KIAA1407 | −4.273546 | −0.4475706 | 7.12E−05 | 9.06E−03 |
| LMBR1L | −4.465177 | −0.4563252 | 3.67E−05 | 5.77E−03 |
| RAB10 | −4.682295 | −0.4721377 | 1.71E−05 | 3.74E−03 |
| INPP5E | −4.342394 | −0.4818347 | 5.62E−05 | 7.84E−03 |
| TANGO6 | −4.287174 | −0.5897189 | 6.79E−05 | 8.75E−03 |
| LCA5 | −4.670828 | −0.6010548 | 1.78E−05 | 3.74E−03 |
| LINC00959 | −4.459301 | −0.6769525 | 3.75E−05 | 5.79E−03 |
| DDHD1 | −5.56089 | −0.7373122 | 6.83E−07 | 3.93E−04 |
| SEMA3F | −5.312191 | −0.8999891 | 1.73E−06 | 7.56E−04 |
| PTGR1 | −5.837171 | −0.9936534 | 2.41E−07 | 1.93E−04 |
| ANKRD33B | −4.583103 | −1.0284012 | 2.43E−05 | 4.52E−03 |
| TRIM61 | −4.522971 | −1.0557596 | 3.00E−05 | 5.20E−03 |
| PSTPIP2 | −4.512212 | −1.0708537 | 3.11E−05 | 5.24E−03 |
| HEBP2 | −4.855401 | −1.1343351 | 9.20E−06 | 2.53E−03 |
| NFIL3 | −5.131065 | −1.1961312 | 3.37E−06 | 1.13E−03 |
| METRNL | −5.367948 | −1.2970141 | 1.41E−06 | 6.73E−04 |
| ZNF585B | −4.475736 | −1.2989619 | 3.54E−05 | 5.69E−03 |
| SERINC2 | −4.669901 | −1.331719 | 1.79E−05 | 3.74E−03 |
| SH2D4A | −4.260014 | −1.3650528 | 7.45E−05 | 9.43E−03 |
| TBC1D2 | −4.483972 | −1.3749573 | 3.44E−05 | 5.66E−03 |
| STEAP2 | −4.300687 | −1.3925252 | 6.48E−05 | 8.52E−03 |
| PTPRB | −4.879853 | −1.4727397 | 8.42E−06 | 2.35E−03 |
| NOTCH3 | −4.51109 | −1.5696335 | 3.13E−05 | 5.24E−03 |
| DUSP1 | −4.785775 | −1.6339789 | 1.18E−05 | 2.97E−03 |
| PRKG1 | −5.26052 | −1.6924671 | 2.09E−06 | 8.60E−04 |
| MAN1A1 | −4.541875 | −1.7979765 | 2.81E−05 | 4.99E−03 |
| LOXL1-AS1 | −5.684096 | −1.8588609 | 4.30E−07 | 2.79E−04 |
| PLAGL1 | −4.482 | −2.4807309 | 3.46E−05 | 5.66E−03 |
| FHL1 | −4.486256 | −2.5086713 | 3.41E−05 | 5.66E−03 |
| FOXP1 | −6.314977 | −2.677233 | 3.86E−08 | 4.56E−05 |
| DSP | −4.654542 | −2.7856211 | 1.89E−05 | 3.83E−03 |
| LOXL1 | −4.807904 | −2.9499098 | 1.09E−05 | 2.81E−03 |
| CDH11 | −4.430404 | −3.3173098 | 4.14E−05 | 6.17E−03 |

Since mRNA expression does not imply functional protein expression, and because micro-environmental IFNγ is known to influence MHC-I, MHC-II and PD-L1 expression, representative cell lines from HLA-DRA-expressing (cluster Ia and Ib, FIG. 1B) and HLA-DRA-deficient (cluster II, FIG. 1B) subgroups were characterized by flow cytometry under basal and stimulated (IFNγ) conditions. Cell surface expression mirrored mRNA expression patterns; MHC-I (HLA-A/B/C) was expressed ubiquitously among all cell lines under both basal and stimulated conditions, while MHC-II (HLA-DR) was present only on the intermediate/Ib (SKMEL5 and SKMEL28) and high/Ia cell lines (WM115 and A375; FIGS. 3A-C and 4A-D). No significant increase in HLA-DR expression was observed with either CHL-1 or HMCB even after 72 hrs of IFNγ treatment (FIG. 4D). Notably, the intermediate/Ib cell line SKMEL28 had a unique population (25%) of cells that was constitutively HLA-DR-expressing at baseline, and was potently induced by IFNγ (FIG. 3D). The high (Ia) WM115 cell line was essentially 100% positive for HLA-DR at both basal and stimulated conditions.

Figure 3A:
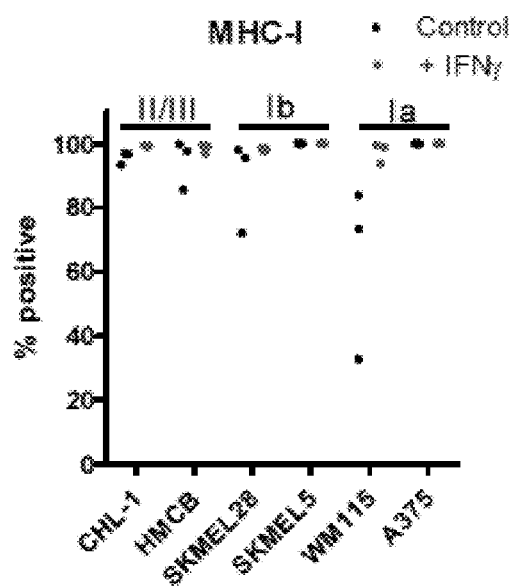
FIGS. 3A-F show characterization of MHC-II(+) melanoma cell lines. Melanoma cell lines were treated with IFNy for 24 h before collection and live-cell staining and flow cytometry analysis for (A) MHC-I (HLA-A/B/C), (B) MHC-II (HLA-DR), and (C) PD-L1. Bars represent mean ±S.E.M. for at least three experiments (D) Representative flow plots from (C). (E) Western blot analysis of melanoma cell lines after 24 or 48 h of IFNy stimulation. (F) Phosphorylation of STAT1 (top row) and STAT5 (bottom row) in melanoma cell lines at 15 min after IFNy stimulation. Histograms were coloured according to the arcsinh transformed ratio or MFI medians relative to the table minimum value.
Figure 3B:
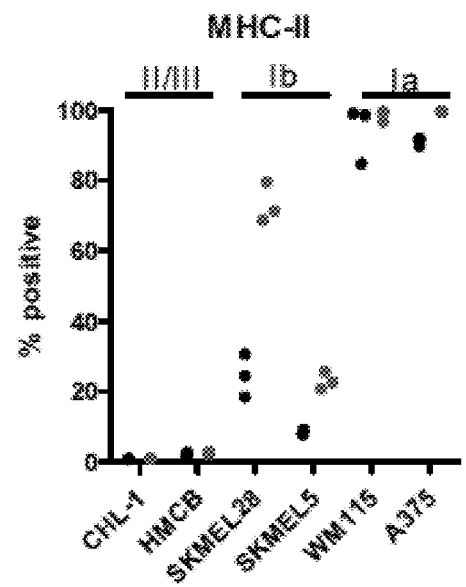
Figure 3C:
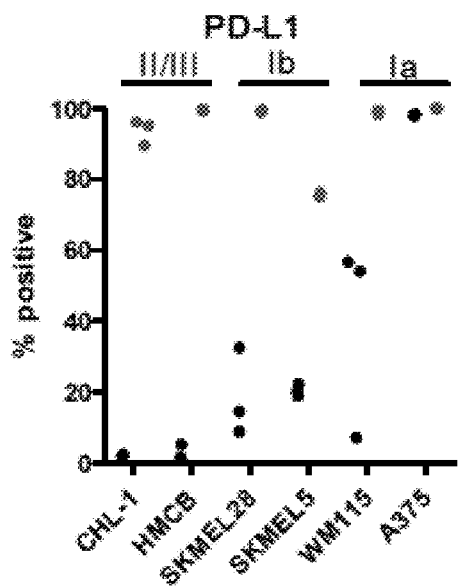
Figure 3D:
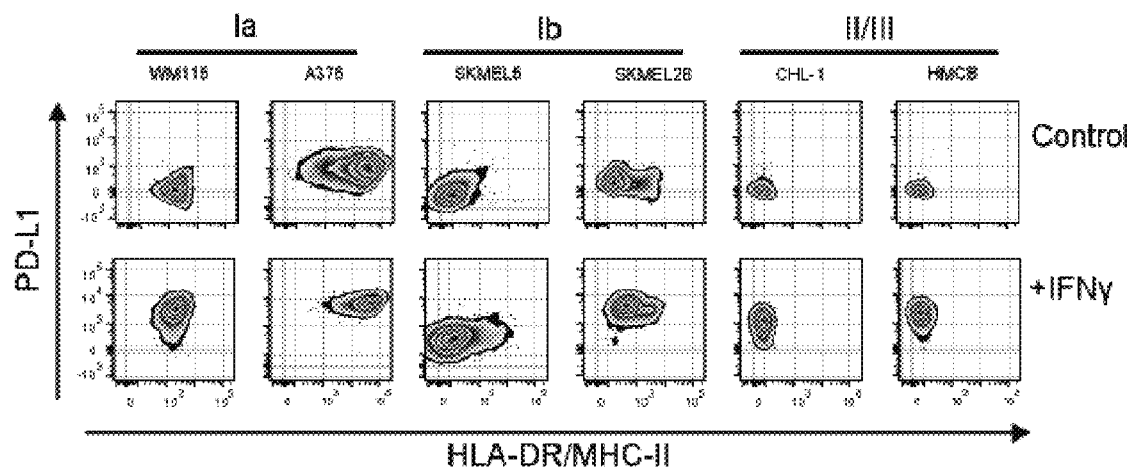
Figure 3E:
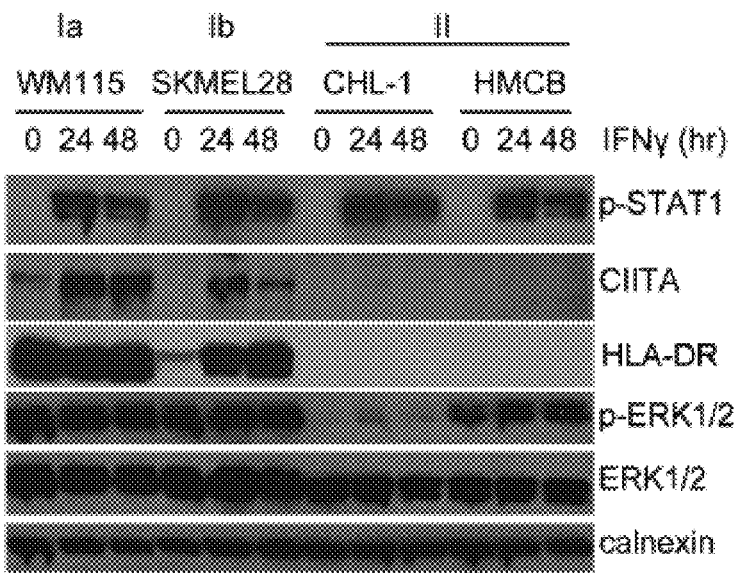
Figure 3F:
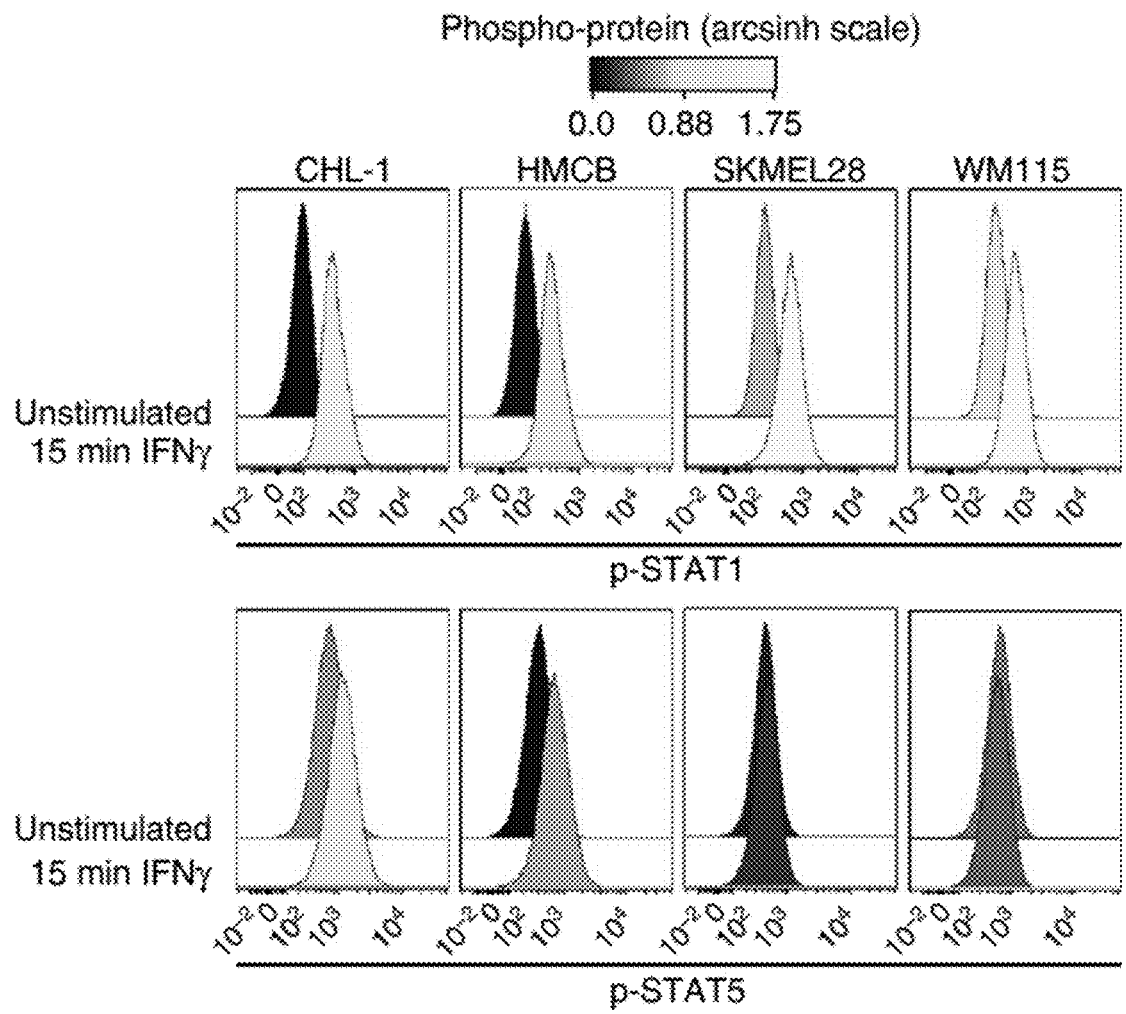
Figure 4A:
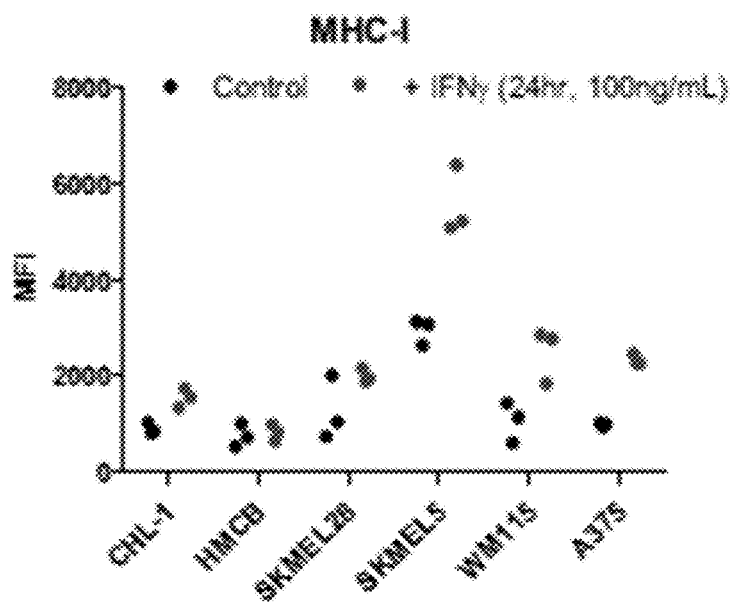
FIGS. 4A-D show graphs illustrating mean expression levels of MHC-I, MHC-II, and PD-L1 at baseline and after IFNy stimulation. Melanoma cell lines were treated with 100 ng IFNy for 24 hr (shown as percentage positive in FIGS. 2A-C) prior to harvest and live-cell staining and flow cytometry analysis for (A) MHC-I/HLA-A/B/C, (B) MHC-II/HLA-DR, and (C) PD-L1. Bars represent mean fluorescence intensity ±SEM for 3 experiments. (D) Histograms of HLA-DR surface expression over an extended (24-72 hr) IFNy treatment, as assessed by flow cytometry.
Figure 4B:
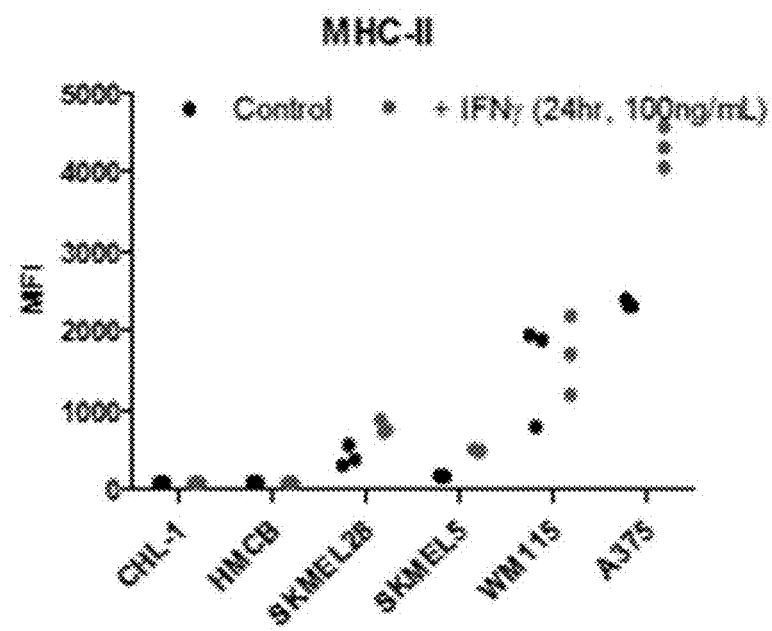
Figure 4C:
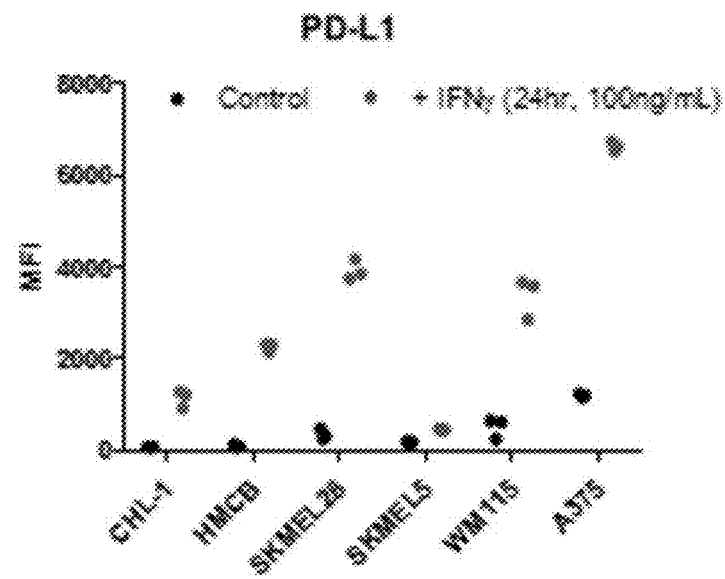
Figure 4D:
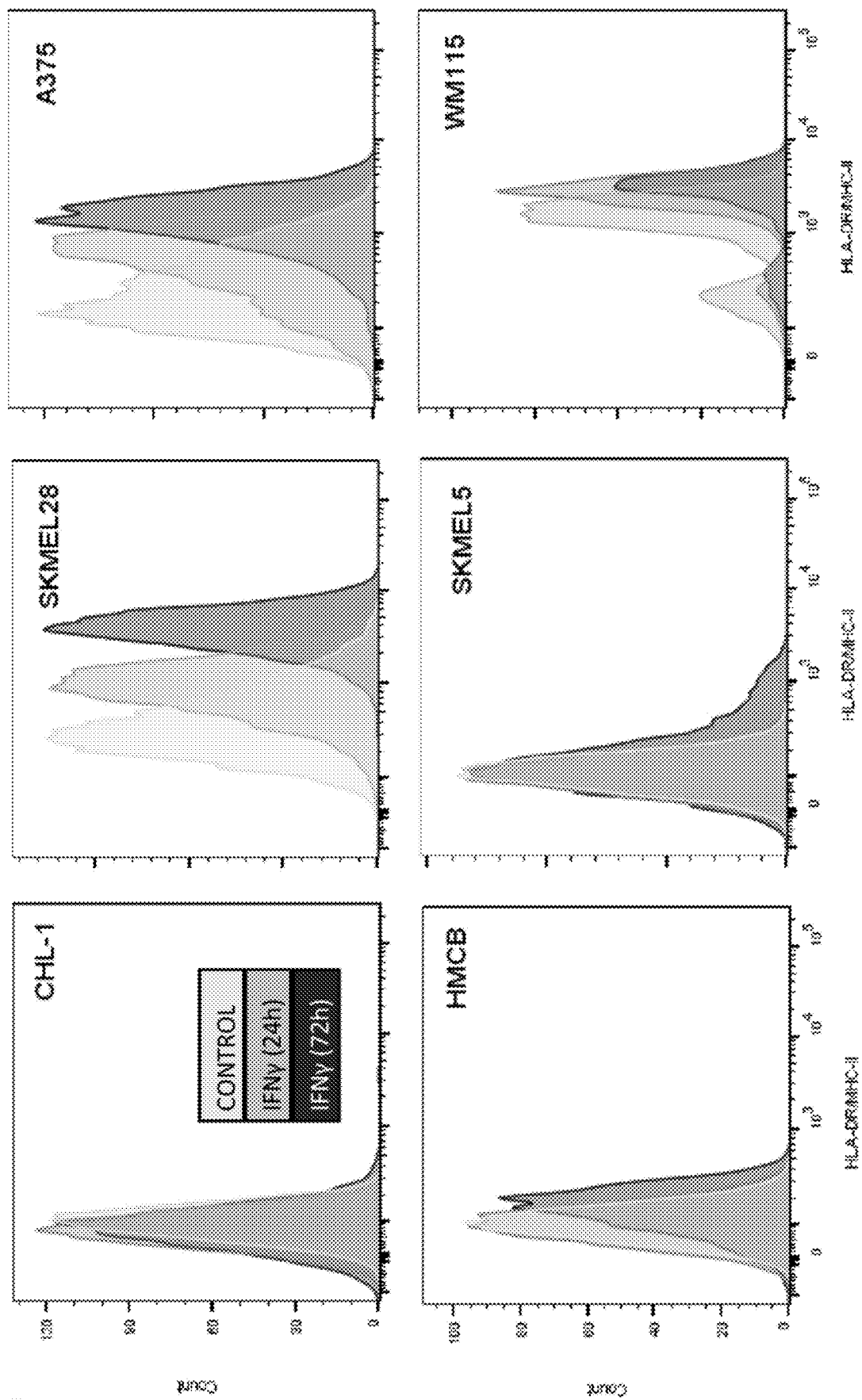

Interestingly, PD-L1 expression was potently induced with stimulation in all cell lines, though the HLA-DR+ cell lines exhibited greater populations of cells that were PD-L1 positive in the absence of IFNγ (FIGS. 3C-D). Consistent with this, STAT1 was robustly activated with IFNγ stimulation in all cell lines whereas CIITA expression, a master regulator of MHC-II transcription, was only induced in HLA-DR+Ia/Ib cells (FIG. 3E). Phospho-flow analysis demonstrated that while STAT1 was activated robustly with short-term (15 min) IFNγ stimulation, STAT5 was preferentially activated by IFNγ in MHC-II(−) cell lines (FIG. 3F), consistent with the observations of others that STAT5 can contribute to resistance to interferon signaling and phenotypes. Together, these results suggest that there is a tumor-cell autonomous inflammatory signal present in a subset of melanomas that may predispose the tumor to enhanced MHC-II expression, antigen presentation (direct or cross-presentation via exosomes) to CD4+ T helper cells, and immune recognition, coinciding with higher PD-L1 expression. Furthermore, these data suggest that STAT5 activation may contribute to suppression of this inflammatory signal. Thus, it was reasoned that the HLA-DR-expressing subtype of melanoma can be unmasked to the immune system by therapeutic inhibition of the PD-1/PD-L1 axis.

Figure 5A:
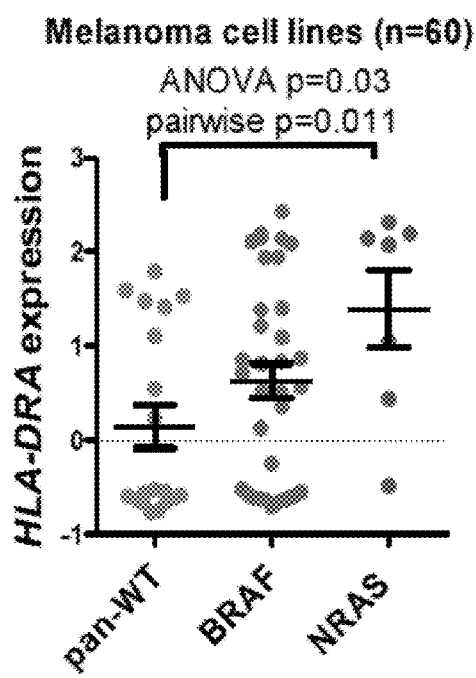
FIGS. 5A-D show MHC-II-positive melanoma cell lines associate with NRAS mutations. (A) HLA-DRA mRNA expression in melanoma cell lines (n=60; one cell line lacked mRNA expression data) from the CCLE compared by genotype. P value (P<0.05) represents result of Tukey's post hoc analysis comparing pan-WT with NRAS-mutant cell lines, following a significant ANOVA (P=0.03) performed among all groups. Bars represent mean±S.E.M. (B) Representative IHC for HLA-DR (brown) and SOX10 (pink) in cases with isolated stromal positivity (top) and with tumour-specific staining (bottom). Both HLA-DR and SOX10 immunostaining is present in all four sections. Scale bar, 50 μm. (C) Analysis of HLA-DR IHC in a melanoma TMA (n=67 evaluable) by genotype. P value represents result of a $\chi^2$-test. (D) Overall survival of patients (n=58 evaluable) within the TMA by HLA-DR status (left censored at time of diagnosis). The remaining patient samples were included from outside institutions and follow-up data were not available from those institutions. P value is the result of the log-rank test.
Figure 5B:
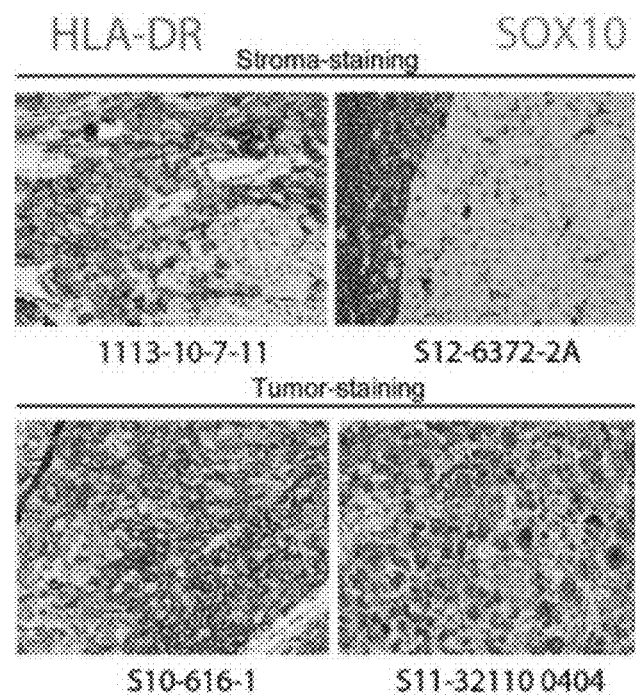
Figure 5C:
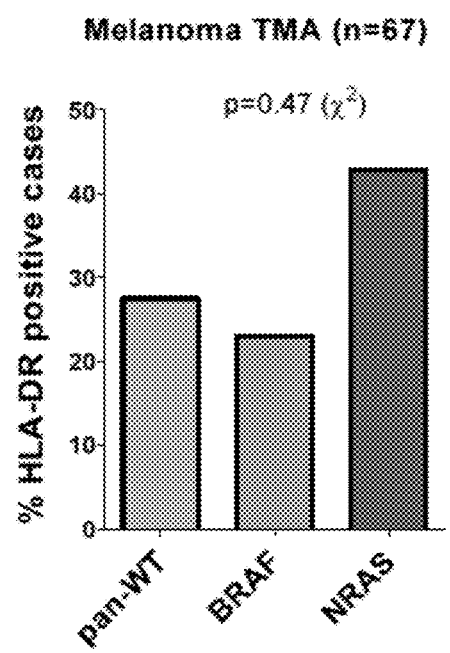
Figure 5D:
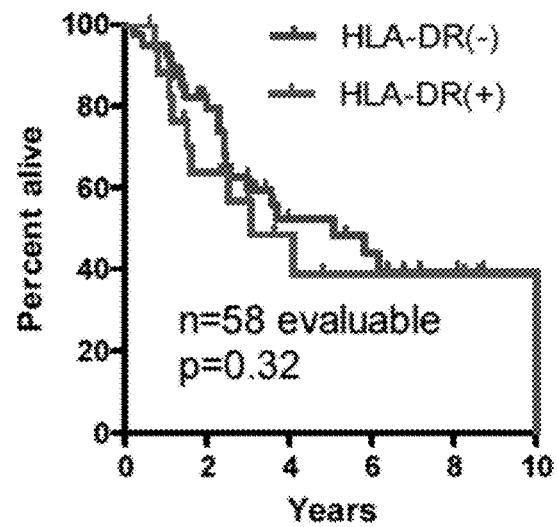

HLA-DR expression by genotype. HLA-DRA expression was specifically enriched in cell lines harboring NRAS mutations (FIG. 5A). Notably, studies by our group and others have suggested that patients harboring NRAS mutations experience improved response rates to PD-1 axis therapy and other immune therapies. Although the biological basis of this correlation remains to be elucidated, these results were intriguing and compatible with our hypothesis. To confirm this clinically, MHC-II/HLA-DR expression by IHC was first investigated in a tissue microarray (TMA) of melanoma patient samples (n=67) with known BRAF and NRAS genotypes who largely had not received immune therapy (Table 2). Dual-color IHC was performed with HLA-DR and SOX10 to distinguish tumor vs. stromal expression of HLA-DR (FIG. 5B). HLA-DR (+) tumor expression was observed in 20/67 (30%) evaluable samples. Similar to cell line RNA analysis, HLA-DR was expressed more frequently in the NRAS-mutated cohort (43%, 6 of 14) than in BRAF-mutated (23%, 3 of 13) and BRAF/NRAS wild type populations (28%, 11 of 39) (FIG. 5C), but this was not statistically significant ($\chi^2$ p=0.47). Thus, NRAS genotype seems to trend with HLA-DR positivity, but this association does not appear to be a significant in patients. A larger analysis would be needed to determine whether this association is apparent in patients. Importantly, in this unselected population of patients, expression of HLA-DR was not associated with overall survival (p=0.32), suggesting that HLA-DR expression may not be generally prognostic in advanced melanoma (FIG. 5D).

TABLE 2

Association of HLA-DR staining on melanoma tissue microarray with clinical variables (N = 66)

| | HLA-DR (+) N = 20 | HLA-DR (−) N = 46 | P value |
|---|---|---|---|
| Age (average, years) | 57.1 | 61.0 | 0.323 |
| Gender | | | |
| Male | 12 (60%) | 31 (67%) | 0.562 |
| Famale | 8 (40%) | 15 (33%) | |
| Stage at resection/biopsy | | | |
| I-II | 2 (10%) | 6 (13%) | 0.755 |
| III | 6 (30%) | 17 (37%) | |
| IV | 12 (60%) | 23 (50%) | |
| LDH Elevated | 2 (10%) | 10 (22%) | 0.149 |
| Mutation | | | |
| BRAF | 3 (15%) | 10 (22%) | 0.485 |
| NRAS | 6 (30%) | 8 (17%) | |
| BRAF/NRAS wild type | 11 (55%) | 28 (61%) | |
| Primary tumor ulceration | 7 (35%) | 15 (33%) | 0.124* |
| Metastatic disease | 18 (90%) | 35 (76%) | 0.192 |
| Liver involvement[#] | 2 (11%) | 14 (40%) | 0.030 |

TABLE 2-continued

Association of HLA-DR staining on melanoma tissue
microarray with clinical variables (N = 66)

|  | HLA-DR (+)<br>N = 20 | HLA-DR (−)<br>N = 46 | P value |
|---|---|---|---|
| Lung involvement# | 10 (56%) | 24 (69%) | 0.349 |
| Brain involvement# | 7 (39%) | 8 (35%) | 0.220 |
| Median survival | 35.0 mo | 35.0 mo | 0.950 |
| 95% confidence interval | 4.3-65.7 mo | 0-78.2 mo |  |

*Ulceration status unknown in 20 patients
Expressed as percentage of patients with metastatic disease HLA-DR expression in patients receiving anti-PD-1/PD-L1. The instant inventors previously observed that in a diverse collection of melanoma cell lines, patterns of HLA-DR expression were 1) constitutively high, 2) heterogeneous, but inducible by IFNγ, or 3) constitutively off. Similar patterns were observed in a cohort of unselected melanoma tumors, and thus it was hypothesized that these patterns may be predictive of benefit to immunotherapy.

To test this hypothesis, patient-derived xenograft (PDX) models were utilized from the tumor resections of two melanoma patients who subsequently received anti-PD1 therapy; patient 1 (PT1; non-responder, 0% HLA-DR-positive, class II/III) and patient 2 (PT2; partial responder, heterogeneous 15% HLA-DR-positive, class Ib) (FIG. 6A). In PT2, the HLA-DR staining pattern was clearly positive at the invasive interface, suggesting immune-reactivity in this particular tumor, in contrast to other tumors identified in the TMA study which were MHC-II(+) throughout the tumor. The resected tumors from PT1 and PT2 were serially transplanted to athymic nu/nu mice, which are highly deficient in functional T cells, ruling out a possible source of IFNγ (FIG. 6B). Immunohistochemistry analysis of both PDX models, grown in nude mice, demonstrated no detectable HLA-DR expression (data not shown). However, when PDX tumors were freshly resected, sectioned and grown ex vivo as cultured tissue slices, in the presence or absence of IFNγ, only the PT2 PDX model (anti-PD-1 responder) upregulated HLA-DR (FIG. 6D). Thus, HLA-DR may be a marker of IFNγ activity in the microenvironment of some (but not all) tumors. Furthermore, this experiment supports the notion that the IFNγ response varies significantly among melanomas, and demonstrates tumor-autonomous features. Furthermore, these data suggest that HLA-DR expression in melanoma cells may be a biomarker for tumors primed with activated T-cells and an appropriate IFNγ response to mediate sensitivity to PD-1/PD-L1 blockade. Importantly, however, these data do not rule out the existence of melanomas constitutively-expressing HLA-DR in the absence of IFNγ stimulation, as is observed in a significant number of melanoma cell line models (FIG. 1).

In order to determine whether MHC-II expression on melanoma tumors is associated with clinical response to PD-1/PD-L1 targeted therapy, we obtained archival pre-treatment biopsy or resection specimens from 30 patients treated with anti-PD-1 (nivolumab, pembrolizumab) or anti-PD-L1 (MPDL3280A; n=2). The median age was 56 years, the median number of prior therapies was 1, and 14 (47%) had failed ipilimumab (Table 3). Twenty-three patients (77%) had stage IV M1c disease and 12 (40%) had elevated serum lactate dehydrogenase (LDH).

TABLE 3

Clinical characteristics of patients treated with anti-PD-1/PD-L1 (Discovery cohort, n = 30)

|  | Number | Percentage |
|---|---|---|
| Age | 56 (median) | 27-81 (range) |
| Gender |  |  |
| Male | 16 | 53 |
| Female | 14 | 47 |
| Stage |  |  |
| M1a | 3 | 10 |
| M1b | 4 | 13 |
| M1c | 23 | 77 |
| LDH Elevated | 12 | 40 |
| Mutation |  |  |
| BRAF V600 | 6 | 20 |
| NRAS Q61 | 7 | 23 |
| BRAF/NRAS wild type | 17* | 57 |
| Prior therapies | 1 (median) | 0-3 (range) |
| IL-2 | 5 | 20 |
| Ipilimumab | 14 | 47 |
| BRAF +/− MEK inhibitor | 4 | 13 |
| Cytotoxic chemotherapy | 5 | 17 |

*NRAS status unknown on 2 patients

MHC-II+ from MHC-II− samples were differentiated using a cutoff of >1% of tumor (SOX10+) membranes showing staining. However, the vast majority of positive samples were positive in greater than 5% of tumor cells in the entire section; only one positive sample within the cohort scored at the 2% range. HLA-DR staining strongly correlated with response to therapy. Among 14 patients with positive HLA-DR staining (>1% estimation of positive tumor membranes in the entire tissue section), 11 patients (79%) had complete (n=3) or partial (n=8) response (FIG. 7A). Clinical activity was inferior in HLA-DR non-expressing melanomas; 6 of 16 patients (38%) responded to therapy (ORR 79% vs. 38%, Fisher's Exact p=0.033). Clinical benefit (including mixed responses) was similarly superior in MHC-II(+) patients (Fisher's Exact p=0.007). Importantly, this finding was confirmed in a second independent dataset of 23 melanoma patients treated with anti-PD-1 therapy (single agent or concurrently with other immunotherapies). Of these 23 additional patients, 6/8 (75%) of HLA-DR(+) tumors responded (PR or CR), while only 4/15 (27%) HLA-DR(−) responded (Fisher's Exact p=0.025) (FIG. 7B). Rapid objective clinical responses were observed in HLA-DR(+) tumors, even in patients with other negative prognostic features, including a patient with bulky disease, elevated LDH, impaired functional status, and failure of both ipilimumab and dabrafenib/trametinib, and a patient with a >10 cm liver mass and LDH>500 unit/L following failure of interleukin-2 and ipilimumab (FIG. 7C).

Figure 7D:
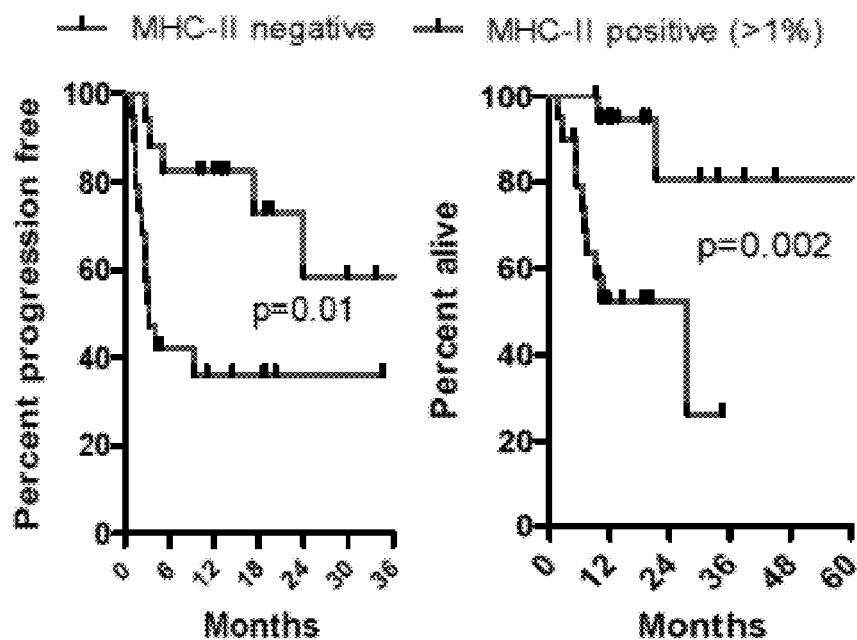
Figure 8:
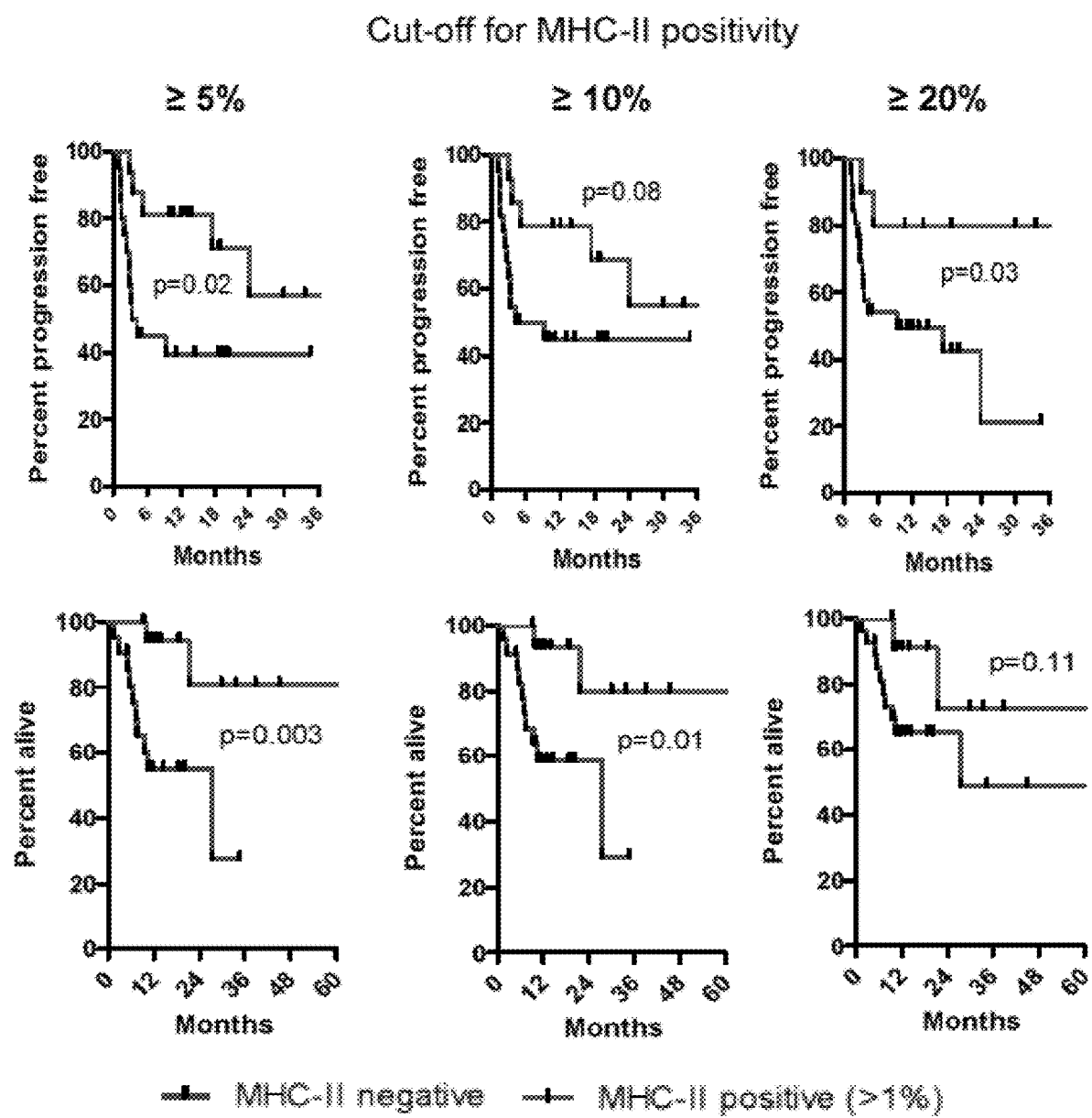
FIG. 8 shows graphs illustrating progression-free and overall survival as a function of MHC-II positivity cutpoints. Statistical significance of PFS (top) and OS (bottom) were assessed by the log-rank statistic using different cutpoints for HLA-DR positivity (5%, 10%, and 20% of tumor cells positive).
Figure 9:
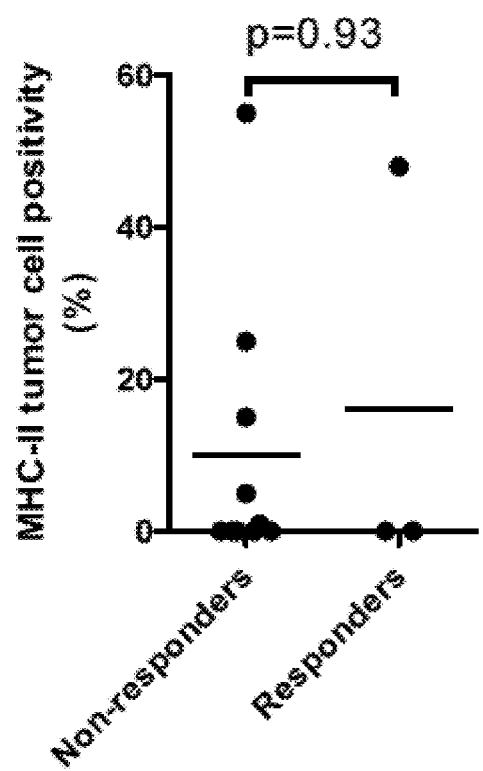
FIG. 9 shows a graph illustrating that MHC-II/HLA-DR positivity is not associated with ipilumumab response. Tumor membrane-specific HLA-DR expression quantified by IHC in excisional samples from patients (n=13) treated with ipilumumab (after tissue collection) were compared to treatment response. P-value represents the result of the Wilcoxan rank sum test for all responder groups versus non-responders (PD).

Progression-free survival (PFS) between patient groups in both datasets was also compared, when survival data were available. The median PFS was superior in the HLA-DR (+) group (median not reached vs. 3.2 months, log-rank p=0.01; FIG. 7D). Overall survival was also superior for the HLA-DR (+) cohort (median not reached vs. 27.5 months, log-rank p=0.002; FIG. 7D). The 3 patients with mixed responses from the PFS analysis (given difficulties specifying time of clinical progression), but not the OS analysis, were excluded. Importantly, statistical significance or a trend toward significance was retained at other cut-points as well, including 5%, 10%, and 20% (PFS log-rank p=0.02, p=0.08, and p=0.03, respectively and OS log-rank p=0.003, p=0.01, and p=0.11, respectively; FIG. 8). Notably, an association with HLA-DR expression and response among 13 patients treated with ipilimumab alone was not observed, although the sample size is too small to make definitive conclusions (FIG. 9 and Table 4).

TABLE 4

Clinical characteristics of patients treated with ipilimumab (n = 13).

|  | Number | Percentage |
|---|---|---|
| Age | 56 (median) | 34-79 (range) |
| Gender |  |  |
| Male | 6 | 62 |
| Female | 5 | 38 |
| Stage |  |  |
| M1a | 1 | 6 |
| M1b | 2 | 15 |
| M1c | 10 | 77 |
| LDH Elevated | 5 | 38 |
| Mutation |  |  |
| BRAF V600 | 3 | 23 |
| NRAS Q61 | 3 | 23 |
| BRAF/NRAS wild type | 7 | 54 |
| Prior therapies | 0 (median) | 0-3 (range) |
| IL-2 | 0 | 0 |
| Anti-PD-1/PD-L1 | 1 | 8 |
| BRAF +/− MEK inhibitor | 1 | 8 |
| Cytotoxic chemotherapy | 2 | 15 |

Figure 10A:
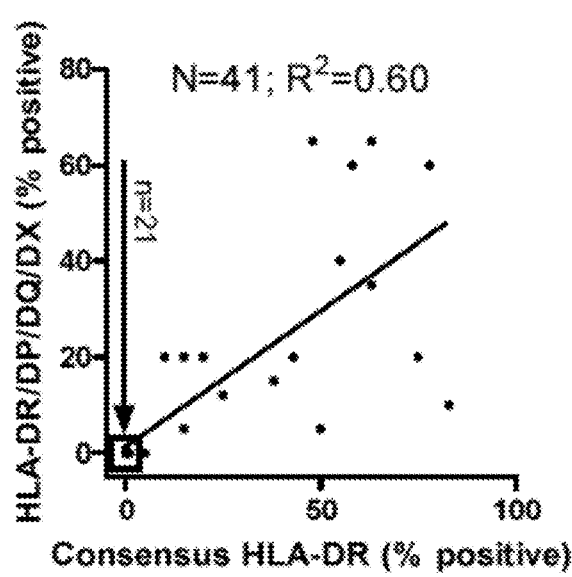
FIGS. 10A-D show graphs illustrating high correlation of staining for two independent monoclonal antibodies for MHC-II in melanomas. (A) forty-one (41) melanoma sections were co-stained for HLA-DR and SOX10 or HLA/DR/DP/DQ/DX and SOX10 and percent of tumor cells in the entire section with MHC-II(+) membranes were calculated. There was a high degree of concordance between staining for the two antibodies. There are 21 data points at (0,0). (B) HLA-DR/DP/DQ/DX positivity was used to test for association with clinical response as described for FIGS. 7A-B. P-value is the result of the Wilcoxan rank sum test. (C) and (D) PFS and OS respectively, in 26 patients (Discovery set only, non-evaluable stains excluded) discriminated on MHC-II (HLA-DR/DP/DQ/DX positivity, using a 5% cut-point (5% of total tumor cells staining positive on the entire section; no tumors stained between 1-5%). P-value represents the result of the log-rank test.
Figure 10B:
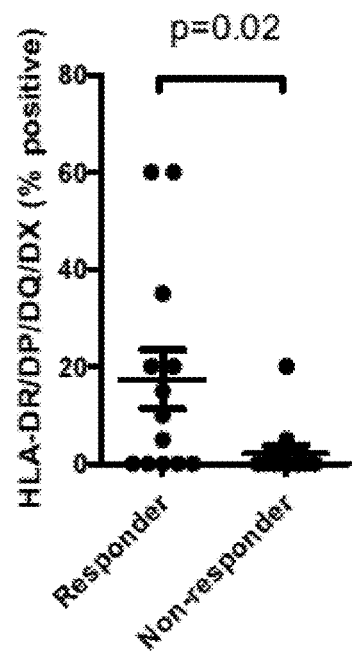
Figure 10C:
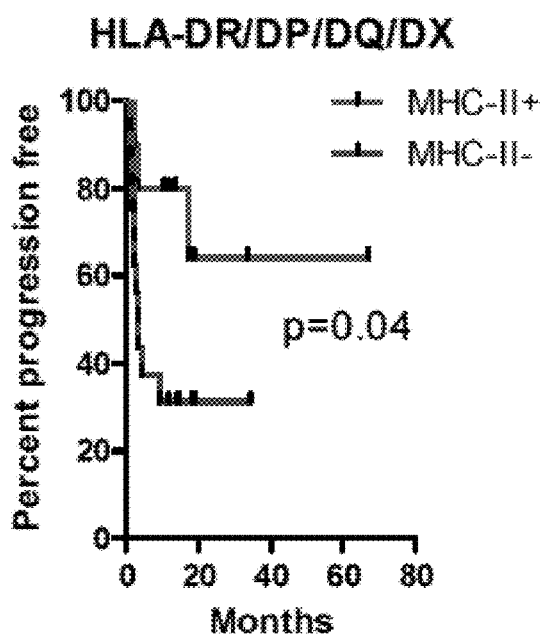
Figure 10D:
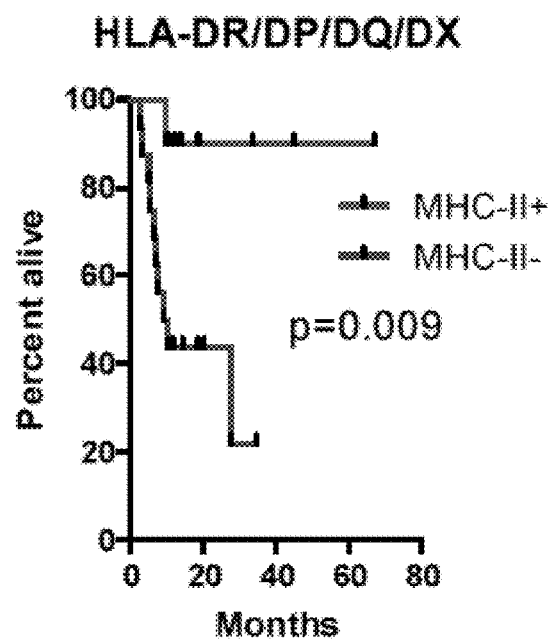

MHC-II antibody specificity and concordance of assessment. To investigate the possibility of alternative MHC class II molecule expression, IHC was performed using a second monoclonal antibody targeting a common epitope to HLA-DR-DP-DQ and -DX (pan-MHC-II) on all samples. Results largely correlated with HLA-DR (FIGS. 7E and 10A), supporting high specificity of the HLA-DR antibody. No additional cases were identified as MHC-II(+) by use of the pan-MHC-II antibody. Pan-MHC-II positivity was also associated with objective clinical response (Mann-Whitney's p=0.02, FIG. 10B) as well as PFS and OS using a 5% cut-point (log-rank p=0.04 and p=0.009, respectively; FIGS. 10C-D). Concordance in HLA-DR positivity assessment between two independent blinded pathologists was 77%. After web-mediated discussion of the discordant cases, a final consensus was reached. Concordance and consensus results of the two independent scores for HLA-DR are presented in Tables 5 and 6, respectively.

TABLE 5

Concordance of HLA-DR positivity between two clinical pathologists blinded to study results (IPI and anti-PD-1/PD-L1 treated patients)

| | | Investigator 2 impression | | | |
|---|---|---|---|---|---|
| Concordance | | Negative | Positive | Equivocal | Not evaluable |
| Invest-igator 1 im-pression | Negative | 33 | 7 | 0 | 1 |
| | Positive | 5 | 22 | 0 | 0 |
| | Equivocal | 0 | 5 | 0 | 0 |
| | Not evaluable | 2 | 1 | 0 | 2 |

TABLE 6

Consensus of HLA-DR positivity between two clinical pathologists blinded to study results (IPI and anti-PD-1/PD-L1 treated patients)

| | | Consensus (# of cases) | | |
|---|---|---|---|---|
| Investigator 1 impression | Investigator 2 impression | Negative | Positive | Not evaluable |
| Positive | Negative | 2 | 3 | 0 |
| Negative | Positive | 5 | 1 | 1 |
| Equivocal | Positive | 0 | 5 | 0 |
| Not evaluable | Negative | 0 | 0 | 2 |
| Not evaluable | Positive | 0 | 0 | 1 |
| Negative | Not evaluable | 0 | 0 | 1 |

Figure 7E:
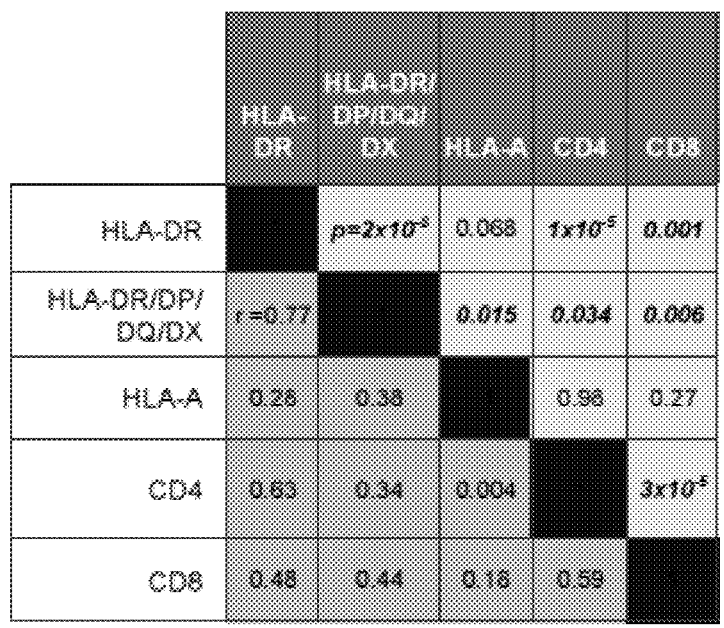
Figure 11:
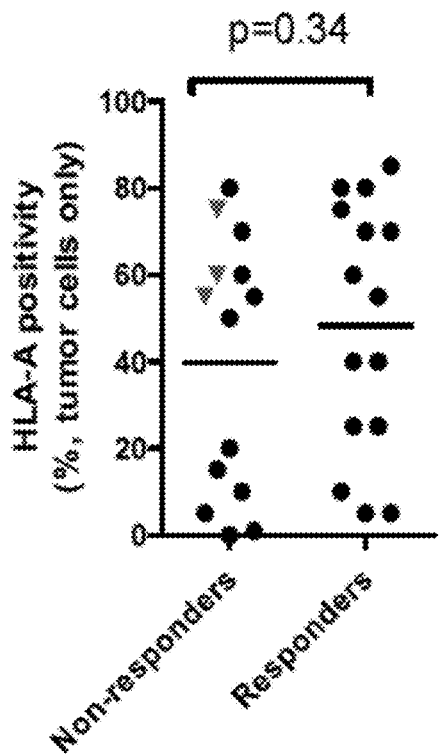
FIG. 11 shows a graph illustrating that MHC-I/HLA-A positivity is not associated with PD-1/PD-L1 targeted therapy response. Tumor membrane-specific HLA-A expression quantified by IHC in excisional samples from patients treated with PD-1/PD-L1 targeted therapy (after tissue collection) is compared to treatment response. P-value represents the result of the Wilcoxan rank sum test for all responder groups versus PD. Mixed responders (n=3) are noted by a red triangle.
Figure 12:
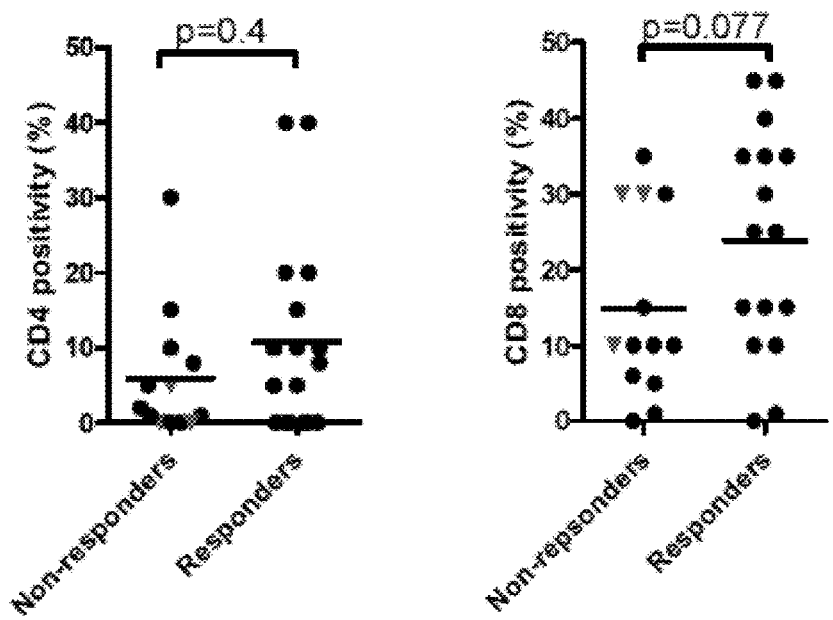
FIG. 12 shows graphs illustrating that CD4 positivity is not associated with PD-1/PD-L1 targeted therapy response. Tumor-infiltrating CD4(+) (left) and CD8(+) (right) cells quantified by IHC in excisional samples from patients treated with PD-1/PD-L1 targeted therapy (after tissue collection) is compared to treatment response. P-values are result of a Wilcoxan rank sum test for all responder groups versus PD. Mixed responders (n=3) are noted by a red triangle.
Figure 13A:
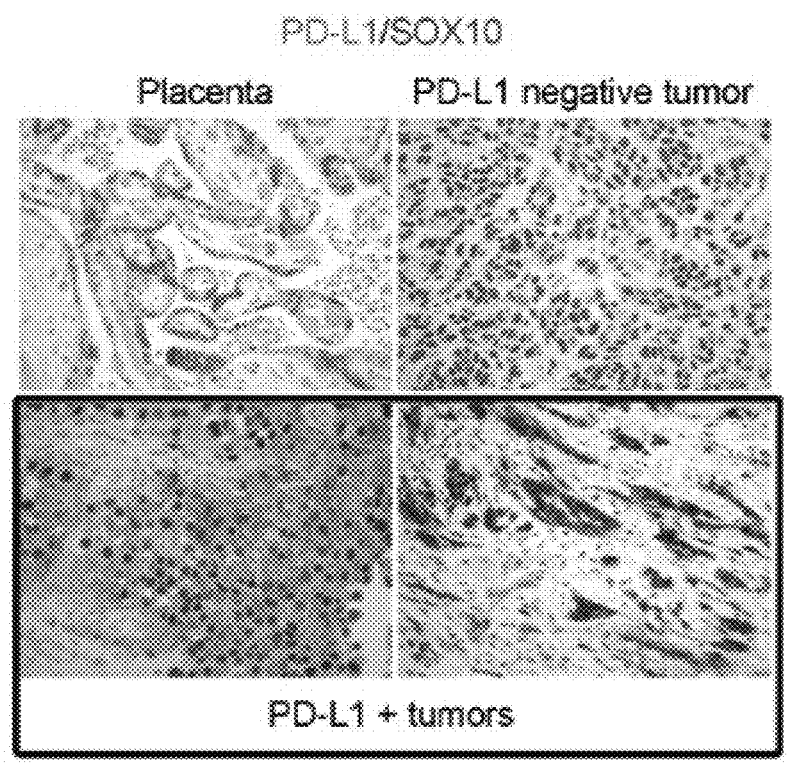
FIGS. 13A-C show graphs and images illustrating a lack of PD-L1 staining with response to PD-1/PD-L1 targeted therapy. (A) representative immunostaining for SOX10 (brown/DAB) and PD-L1 (pink/Warp Red) in human placenta (positive control), a PD-L1(−) tumor, and two PD-L1 (+) tumors. (B) lack of association of PD-L1 positivity with response in a series of 24 anti-PD-1/PD-L1-treated melanoma patients. Only 4/24 patients had PD-L1 positivity noted in the tumor compartment. (C) lack of correlation between tumor cell positivity of PD-L1 and HLA-DR by IHC staining.
Figure 13B:
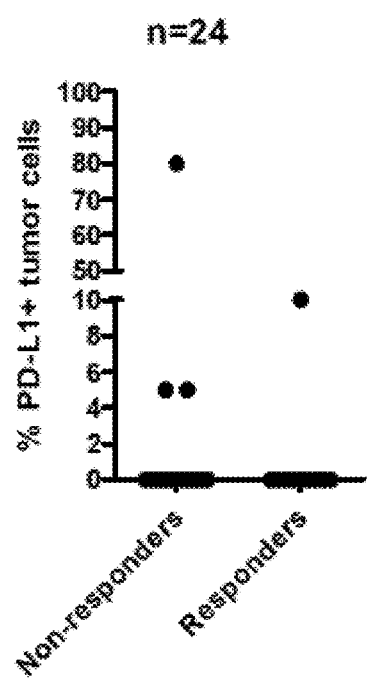
Figure 13C:
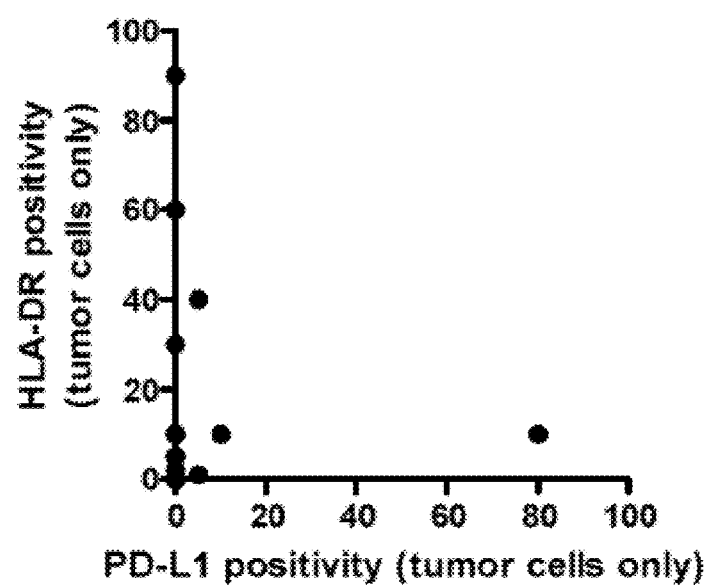

Other Clinical Correlates. To investigate the impact of MHC class I expression on response to anti-PD-1/PD-L1, HLA-A IHC was performed on the same pre-treatment samples. As observed in melanoma cell line models, HLA-A expression was nearly ubiquitous across all tumors and expression level was not statistically associated with response to therapy (FIG. 11). CD4+ and CD8+ T-cell infiltration was also assessed by IHC. CD4 was not statistically associated with therapy response, while a trend toward significance was detected with CD8 (Mann-Whitney's p=0.077; FIG. 12), as has been previously described. The lack of statistical association in the study may be due to scoring method, as the invasive front of the tumor was not detectable in all biopsies or resection specimens. Thus, the total percent positivity of CD8+ T cells invading into the tumor was calculated. Interestingly, the percentage of infiltrating CD4+ T cells were more strongly correlated with HLA-DR expression (Pearson's r=0.63; p=1×10$^{-5}$), while CD8+ infiltrate was more weakly correlated (Pearson's r=0.48; p=0.001)(FIG. 7E). Although HLA-DR and CD4+ infiltrate are biologically connected, association of HLA-DR with CD8 infiltrate may be suggestive evidence that enhanced CD4+ Th infiltrate could support the continued accumulation of CD8+ CTLs in the tumor microenvironment. In the instant cohort, PD-L1 immunostaining in the tumor compartment was rare, occurring in 4/24 (17%) tested patients, and showed no correlation with response to PD-1/PD-L1 targeted therapy (FIGS. 13A-C)

Discussion

Targeting the PD-1/PD-L1 signaling axis produces durable responses in a subset of melanoma patients. Although a genetic basis for clinical response to CTLA-4 inhibition in melanoma has recently been suggested, so far few studies have suggested a tumor-cell autonomous basis for response to PD-1/PD-L1 monoclonal antibodies. Herein, a unique inflammatory transcriptional signature in melanoma cell lines that can be identified by tumor cell-specific MHC-II/HLA-DR expression has been identified. Interestingly, heterogeneity in MHC-II expression among panels of melanoma lines has been previously noted. Without wishing to be bound by theory, it is believed that MHC-II expression is either 1) a functional antigen-presenting molecule that can promote CD4 T helper cell aid to the antitumor milieu or 2) a non-functional marker of the inflammatory state of the cell or tumor milieu. The presence of heterogeneity among cell lines grown ex vivo argues against the latter. Yet another alternative hypothesis is that MHC-II expression on melanoma cells could be instrumental in promoting Treg differentiation in a process that requires PD-1/PD-L1 interaction; thus interruption of this signaling could be beneficial in MHC-II+ tumors. Although different CD4 subsets (Th1, Th2, Th17, Treg) were not assessed, superior clinical out-comes with anti-PD-1/PD-L1 therapy was nonetheless observed in patients harboring melanomas with MHC-II expression. A limited analysis of FoxP3 staining in 10 specimens from the cohort with CD4 positivity showed no association of FoxP3 or FoxP3:CD4 ratio with response to PD-1-targeted therapy or with HLA-DR tumor cell positivity (data not shown).

In a bioinformatics analysis of MHC-II expression in melanoma cell lines, which rules out contaminating stromal and immune contribution, a number of gene expression pathways were found to be up-regulated in melanoma cell lines expressing MHC-II (FIG. 1C). The majority of these pathways suggested the presence of an inflammatory signature and reflected gene sets found to be upregulated in response to viral ("WIELAND UP BY HBV INFECTION"), parasitic infections ("KEGG LEISHMANIA INFECTION"), and auto-immune disease ("KEGG GRAFT VERSUS HOST DISEASE", "KEGG ALLOGRAFT REJECTION", "KEGG ASTHMA", and KEGG AUTOIMMUNE THYROID DISEASE$\leqslant$). Biologically, these pathways reflected stimulation of T-cell receptors ("REACTOME TCR SIGNALING", and "COSTIMULATION BY THE CD28 FAMILY") and B-cell activation ("BIOCARTA BLYMPHOCYTE PATHWAY" and "KEGG INTESTINAL IMMUNE NETWORK FOR IGA PRODUCTION"). Although several gene sets were statistically down-regulated in MHC-II(+) cell lines, visual inspection of the heatmap suggested that these associations were primarily driven by high expression of target genes in a subset of MHC-II(−) cell lines, specifically Cluster II (FIG. 1C).

Although MHC-I is ubiquitously expressed in most cell types, MHC-II is typically restricted to the immune system, as the MHC-II pathway is thought to utilize extracellular antigens (released from apoptotic or necrotic cells and engulfed by professional APCs). However, tumor-specific MHC-II expression has been noted in a number of malignancies, including breast, colon, and melanoma. Experimentally, MHC-II(+) epithelial cells can present antigen to CD4(+) T-helper cells and enforced expression of MHC-II in tumor cells can promote anti-tumor immunity and tumor rejection in vivo. Collectively these data support a role for aberrant HLA-DR/MHC-II expressing tumors as being a uniquely immunogenic subtype (with the ability to stimulate CD4(+) T-helper cells) which may adapt by expressing PD-L1. Thus, although some MHC-II(−) tumors may express PD-L1, this alone may not permit anti-tumor immunity through PD-1/PD-L1 inhibition.

In this study, HLA-DR expression strongly correlated with response to anti-PD-1. Critically, other relevant variables also co-occurred with HLA-DR expression, demonstrated through in silico cell line analysis (Gene Set Analysis, total somatic mutational burden), flow cytometry of well-characterized melanoma cell lines (PD-L1 expression and CIITA expression), and pre-treatment melanoma samples (CD4 and CD8 T cell infiltration). Together, these data strongly argue that HLA-DR plays a causal or correlative role in anti-PD-1/PD-L1 responses. Interestingly, HLA-A expression did not statistically correlate with CD8 expression in the study (FIG. 7E). This could be due to more ubiquitous expression of HLA-A among the tumors, and it could be that the spectrum of MHC-I neo-antigen may be the rate-limiting step in this association. However, MHC-II expression on the tumor did correlate with CD4 infiltrate, though the nature or composition of these CD4+ cells is not yet understood (Th1, Th2, Th17, or Tregs). Furthermore, in this study, only HLA-A was assessed for MHC-I. Additional contributing effects of HLA-B and HLA-C as well as non-classical MHC-I proteins were not assessed in this study due to limitations in robust antibodies and amount of tissue available for analysis.

Although data point toward a functional role of MHC-II expression as contributing to sensitivity to PD-1/PD-L1 axis inhibition, it is important to note that some tumors responded to PD-1 targeted therapy, despite having no detectable MHC-II expression. There are several possible explanations for this observation: 1) that tumor sampling heterogeneity limited our ability to detect HLA-DR in the tumor and/or 2) that these tumors may be similar to the Ib (Interferon-inducible) group and PD-1 inhibition in these patients may increase CD8 infiltration and local IFNγ secretion, inducing HLA-DR, which could be detected by an on-treatment assessment. Of course, this is hypothetical, and also assumes that HLA-DR is a functional biomarker, rather than a surrogate, which remains to be experimentally proven. Yet a third hypothesis would be that other inflammatory/antigenic factors mediated by MHC-I (such as mutational burden and neo-antigen presence) could be sufficiently high in some cases to circumvent or abrogate an MHC-II requirement. Nonetheless, the potential role of MHC-II as a surrogate biomarker for response cannot be overlooked.

Figure 14A:
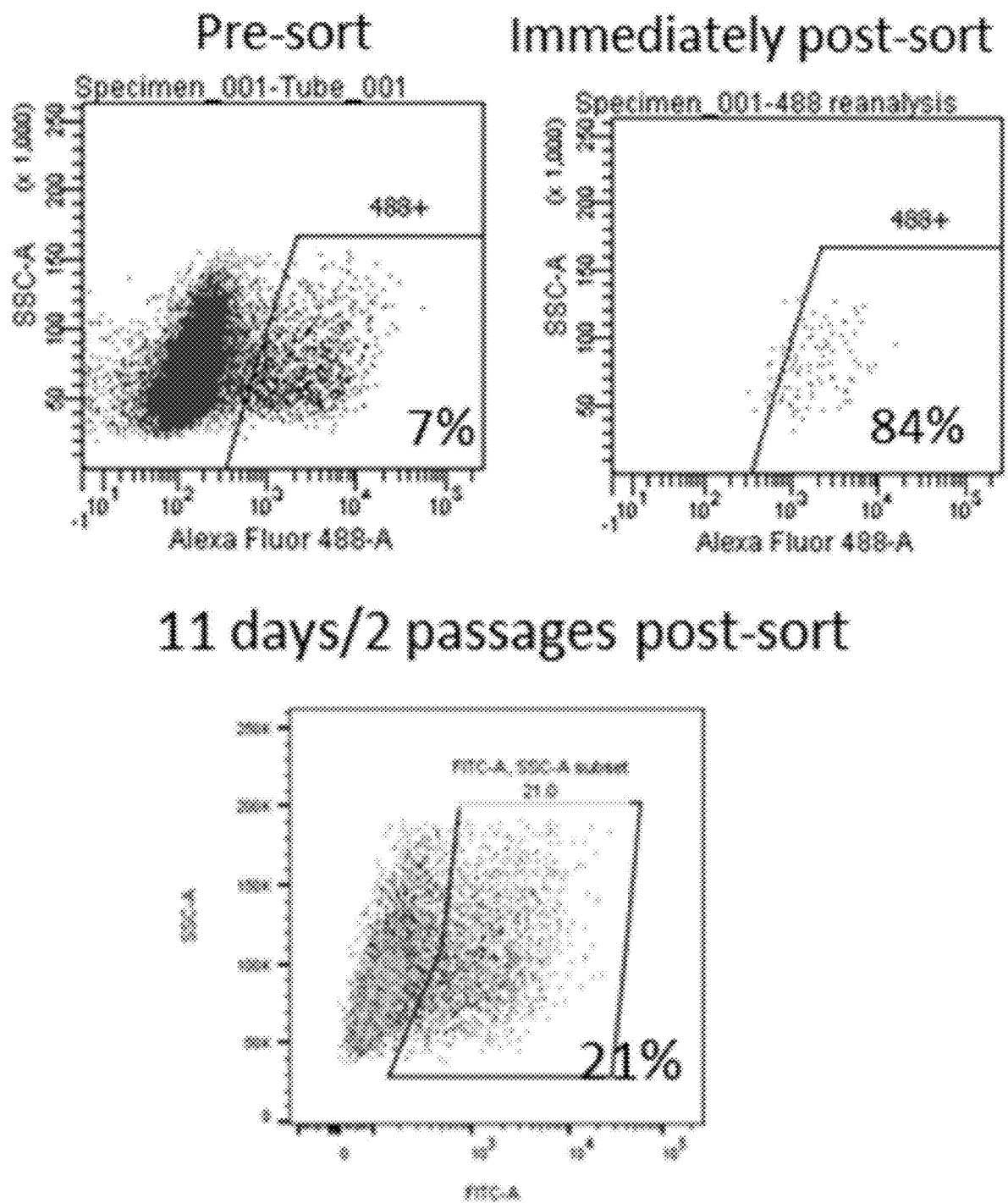
FIGS. 14A-B show graphs illustrating that constitutive expression of MHC-II is selected against in B16 cells, but may have a functional role in response to anti-PD-L1 targeted therapy. (A) flow cytometry sorting of B16/F0 melanoma cells (anti-IA/IE) after lentiviral transduction with mouse Ciita. LACZ was used as a control for lentiviral transduction. After sorting, the percent of MHC-II+ cells was rapidly selected against in culture, despite negative selection with puromycin. (B) lentivirally-transduced cells (50,000 LACZ or Ciita) were injected subcutaneously into the flanks of C57/BL6 mice, which were subsequently treated twice weekly with 100 µg/100 µL anti-mouse PD-L1 mAB (BioXcel) intraperitoneally beginning on day 1 after tumor challenge. For tumor challenge, 3 separate experiments were performed for Ciita+ cell injections (assessed by flow cytometry at the day of injection as containing 10, 20, or ~30% MHC-II/IA/IE+ cells). Tumor volume was measured thrice weekly. Survival curves combined all cohorts of Ciita+ injected mice. Tumor ulceration or tumors exceeding 1000 mm$^{\#}$ was used as an endpoint for survival.

In order to demonstrate a functional role of MHC-II in promoting response to PD-1/PD-L1 therapy, Ciita was over-expressed in B16/F0 melanoma cells to determine whether constitutive tumor cell MHC-II expression would enhance response to PD-L1 mAB in vivo. Despite previous reports of successful constitutive MHC-II (IA/IE) expression by lentivirally-mediated Ciita overexpression, the instant inventors were unable to establish a stable population of MHC-II+ cells in culture, despite repeated rounds of selection and flow sorting (FIG. 14A). Expansion of the positive population in cell numbers sufficient for the experiment routinely caused the MHC-II+ population to degrade to near 1-2% after 3-5 passages. The reason for this selection is presently unclear but is a matter of current investigation. Possible explanations are silencing of the lentiviral promoter or cell-mediated internalization of MHC-II.

Figure 14B:
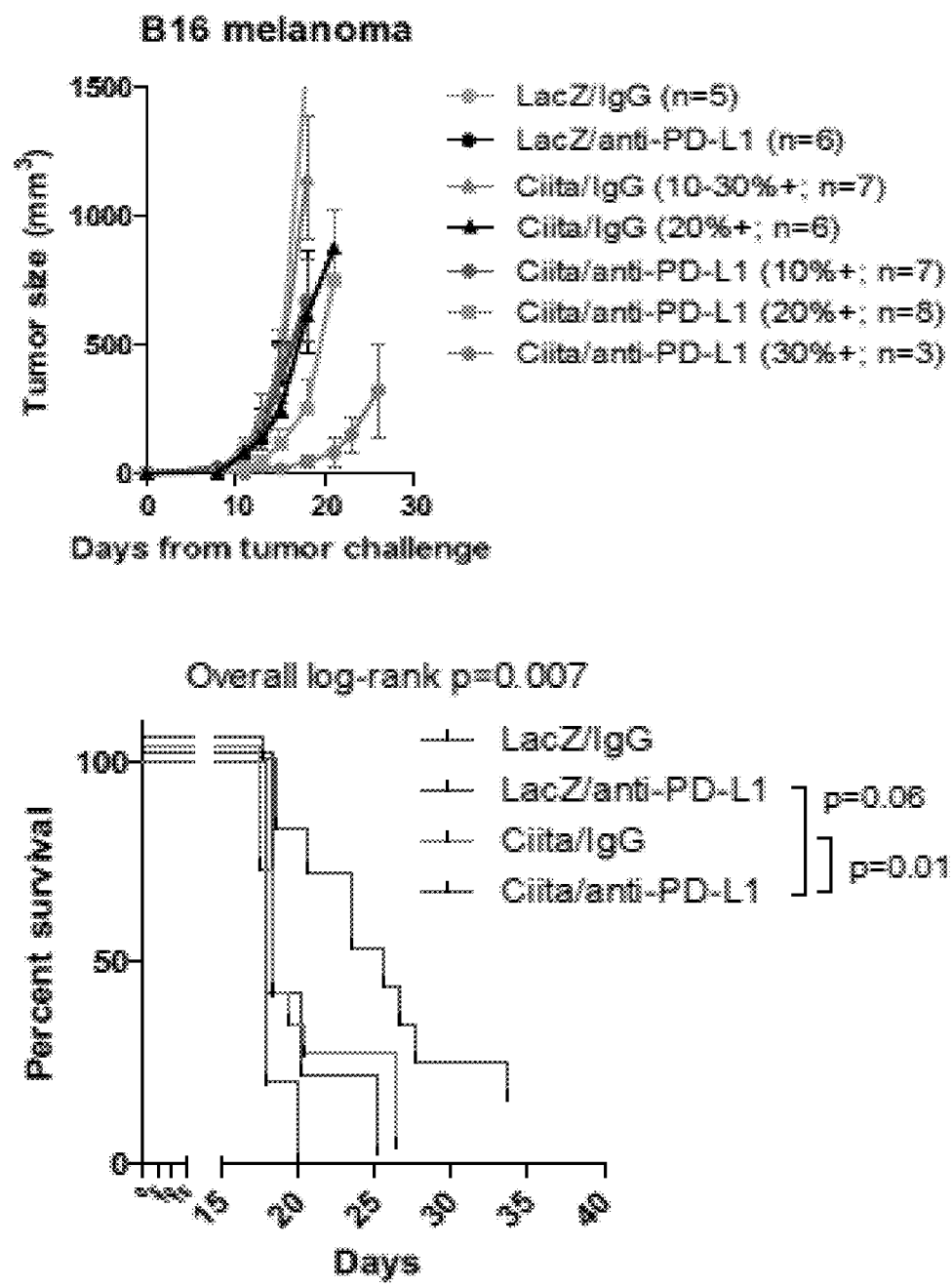

Nonetheless, we injected either control (LacZ-expressing) or Ciita/MHC-II+ B16 cells (ranging from 10-30% MHC-II+ at the time of injection) into the flank of C57/B16 mice and monitored tumor growth and survival with either IgG (isotype) control or anti-PD-L1 mAB, given twice weekly, beginning on day +1 following tumor cell challenge. The subgroup of Ciita+ B16 melanoma cells with the highest degree of MHC-II positivity (30%) at the time of injection, treated with anti-PD-L1, had slower tumor formation and prolonged survival, although the effect was marginal (FIG. 14B). Without wishing to be bound by theory, it is believed that the observed effect may not have been robust due to unstable expression and rapid selection of Ciita-transduced cells in vitro and in vivo. Interestingly, there appears to be an MHC-II+ dose-effect in response to PD-L1 mAB (i.e. 30% MHC-II+ responded better than 10 or 20%). While these results are difficult to interpret due to difficulty in establishing a pure cell line, they are believed to support a potential functional role of MHC-II expression in immunotherapy response.

Conflicting reports of stromal versus tumor PD-L1 staining, coupled with lack of standardization, proprietary nature, and the difficulties associated with PD-L1 as an IHC antigen have precluded the routine use of this marker in the clinic. In the study, a relatively low number of samples stained positively for PD-L1, despite appropriate positive controls (human placenta). The low proportion of samples with PD-L1 staining and lack of correlation of positivity with patient benefit reinforce the problems of using PD-L1 as a clinical biomarker. In contrast, HLA-DR can be robustly identified on tumor cells through use of dual-color IHC using well-established commercially available antibodies. Thus, it is proposed that with additional validation, melanoma HLA-DR expression may be a rapidly translatable biomarker for patient stratification of PD-1/PD-L1 immunotherapy which can easily be performed in standard pathology laboratories at most institutions at low cost. This marker, if validated, could be envisioned to stratify patients toward anti-PD-1 monotherapy and away from the more toxic but potentially more clinically-active combination of ipilimumab and nivolumab. Furthermore, understanding the biological basis for differential MHC-II expression among melanomas may identify agents that induce MHC-II positivity and can be used in combination with PD-1/PD-L1 targeted therapy to enhance response rates.

Methods

Immunoblotting Immunoblotting was performed as previously described[32] Briefly, cells were washed in cold phosphate-buffered saline, collected and lysed in 1×RIPA buffer (50 mM Tris (pH 7.4), 1% NP-40, 150 mM NaCl, 1 mM EDTA, 0.1% SDS, 0.25% sodium deoxycholate, 5 mM NaF, 5 mM Na3VO4, 10% glycerol, 1M phenylmethyl-sulphonylfluoride and protease inhibitors) for 30 min on ice. Lysates were sonicated for 2-3 s to shear DNA and cleared by centrifugation at 13,200 r.p.m. for 15 min. Protein concentrations of the lysates were determined by BCA assay (Bio-Rad, Hercules, Calif.). Samples were separated by SDS-PAGE and transferred to nitrocellulose membrane. Membranes were blocked with 5% non-fat dry milk or 5% bovine serum albumin in tris-buffered saline with 0.1% Tween-20 for 1 h at room temperature and then incubated overnight at 4° C. with the appropriate antibody as indicated. Following incubation with appropriate horseradish peroxidase-conjugated secondary antibodies, proteins were visualized using an enhanced chemiluminescence detection system. This study was performed using the following antibodies: p-STAT1 (Cell Signaling Technology. #7649, 1:5000) STAT1 (Santa Cruz Biotechnology. #SC592. 1:5000), p-ERK1/2 (Cell Signaling Technology #9101, 1:5000), ERK1/2 (Cell Signaling Technology #9102. 1 5000), CIITA (Cell Signaling Technology #3793, 1:1000) HLA-DR (Santa Cruz, sc-53319., 1:5000).

Standard Flow Cytometry. Flow cytometry was performed using the following antibodies: HLA-DR/PE-Cy7 (Biolegend, clone L243. 1:20). CD274/PD-L1/APC (Biolegend, clone 29E.2A3, 1:200) and HLA-A/B/C-Alexa Fluor488 (1:100, Biolegend, clone W6/32) mouse MHC-II (I-A/I-E 1:20 Biolegend, clone M5/114.15.2). DAPI was used as a viability dye. Samples were analyzed on an Aria III laser system (BD Biosciences)

Phospho-flow cytometry. Melanoma cell lines were treated with Accutase™ (EMD Millipore, #SCR005) for 10 minutes at 37° C. to dissociate them from the plate. Dissociated cell lines were rested at 37° C. in a CO2 incubator for 30 minutes prior to stimulation. After resting, cells were stimulated by adding IFNγ (Cell Signaling) at a final concentration of 100 ng/mL. During signaling, cells were kept in a 37° C. CO2 incubator. After 15 minutes of signaling, cells were fixed for 10 minutes at room temperature with a final concentration of 1.6% paraformaldehyde (Electron Microscopy Services). Cells were then pelleted and permeabilized by resuspension in 2 ml of methanol and stored over night at −20° C. Flow cytometry was performed using the following antibodies: HLA-DR/BV421 (BD Horizon™, clone G46-6, 1:40), p-STAT5/PE-Cy7 pY694 (BD Phosflow™, clone 47, 1:10), and p-STAT1/PerCP-Cy5.5 pY701 (BD Phosflow™, clone 4A, 1:10). Samples were analyzed on a LSRII system (BD Biosciences).

Immunohistochemistry. For HLA-DR (Santa Cruz [sc-53319], 1:1000)/SOX10 (LsBio [LS-C312170], 1:30), HLA-DR-DP-DQ-DX (Santa Cruz [sc-53302], 1:1000)/SOX10, HLA-A (Santa Cruz [sc-365485], 1:1300)/SOX10, and PD-L1(Cell Signaling #13684, 1:500)/SOX10 dual IHC tumor sections were stained overnight at 4° C. with both antibodies. Antigen retrieval was performed using Citrate Buffer (pH 6) using a Biocare Decloaking Chamber. The visualization system utilized was MACH2 (Biocare) using DAB (Dako) and Warp Red (Elmore), and counterstained with hematoxylin.

For CD4 and CD8 staining, slides were placed on a Leica Bond Max IHC stainer. All steps besides dehydration, clearing and coverslipping are performed on the Bond Max. Heal induced antigen retrieval was performed on the Bond Max using their Epitope Retrieval 2 solution for 20 minutes. Slides were incubated with anti-CD4 (PA0427, Leica, Buffalo Grove, Ill.) or anti-CD8 (MS-457-R7, ThermoScientific. Kalamazoo. Mich.) for one hour. The Bond Polymer Refine detection system was used for visualization. CD4 and CD8 were scored as % infiltrating CD4(+) or CD8(+) cells in the tumor area.

HLA-DR scoring determination. Two pathologists (MVE and RS) who were unaware of clinical response data made independent visual estimations of the percentage of tumor membrane-specific positivity for HLA-DR, in SOX10(+) nuclei areas, in the whole tumor section focusing at the tumor hot spots. For all staining batches positive and negative controls (human tonsil; HLA-DR is positive in germinal and non-germinal center cells and negative in squamous epithelial cells) were included and stained appropriately and reproducibly in all cases. Furthermore, nearly all cases had positive-staining stromal cells (presumably B-cells and macrophages) as an internal control. In concordant cases (both investigators scored as 'negative' (1% or less of all tumor cells in the entire tissue section staining positive; i.e. all analyzable fields of view) or 'positive' (>1% of tumor cells in the entire tissue section staining positive; i.e. all analyzable fields of view)), the result was averaged. For discordant cases {i.e. positive vs. negative interpretation, or any concerns on evaluable nature of the specimen) the investigators reviewed the case together to reach a final conclusion or consensus. If no consensus could be agreed upon, the sample was listed as non-evaluable.

Cancer Cell Line Encyclopedia analysis. Gene expression data (Affymetrix hg133plus2) from the Cancer Cell Line Encyclopedia (CCLE) were downloaded from the Broad Institute (broadinstitute.org) and analyzed in R (r-project.org/). RMA-normalized melanoma cell line data were collapsed to the gene level and filtered using the 'genefilter' package. Differentially expressed genes were identified using a t-test with a false-discovery rate correction. Hierarchical clustering was performed using 1-Spearman's rank correlation and complete linkage. Gene Set Analysis was performed using the GSA package in R and the maxmean statistic. Gene sets in the molecular signatures database curated gene sets C2 collection (version 3.0) were utilized for GSA.

Cell and tumor culture. SKMEL-28 and WM115 cell lines were obtained from Dr. Kimberly Dahlman (Vanderbilt University), CHL-1 and HMCB melanoma cell lines were obtained from the laboratory of William Pao (Vanderbilt University). Cell line nature was not directly authenticated, but protein marker expression was consistent with published HLA-DRA mRNA expression patterns (CCLE). Cell lines were confirmed mycoplasma-free and cultured in DMEM containing 10% FBS. Stimulation with recombinant human IFNγ (R&D Systems) was performed at 100 ng/mL. For PDX models and ex-vivo organotypic culture, tumors were freshly resected and sectioned using an Alto tissue matrix sectioner (Roboz Surgical, Gaithersburg, Md.).

Patients. Patient samples and data were procured based on availability of tissue and were not collected according to a pre-specified power analysis. All patients were consented on IRB approved protocols (Vanderbilt IRB #030220 and 100178). Tumor samples for the TMA and for the HLA-DR staining cohort were obtained from tumor biopsies or tumor resections obtained for clinical purposes. Samples were obtained within 2 years of start of anti-PD-1/PD-L1 therapy (nivolumab, pembrolizumab, MPDL3280a). Only patients with available tumor samples and evaluable responses were included. In cases where multiple tissues were available for the same patient, the evaluable sample collected closest to PD-1 therapy was utilized for scoring. Clinical characteristics and objective response data were obtained by retrospective review of the electronic medical record. All responses were investigator assessed, RECIST defined responses or (in a single case) prolonged stable disease with clinical benefit lasting >3 years.

For the validation set, all patients were consented to an IRB-approved tissue banking protocol (for MGH patients as part of either Dana Farber Harvard Cancer Center protocols 02-017 and 11-181). Samples were obtained prior to therapy with anti-PD-1/PD-L1 monoclonal antibodies for research (as opposed to clinical) purposes. A linked database was prospectively maintained and regularly updated with clinical characteristics, response to therapy, date of progression (if applicable), and date of death or last follow up visit.

Statistical analysis. The tests of hypotheses concerning between two groups comparisons were completed using either two-sample Student t-test or non-parametric Wilcoxon rank sum test for continuous variables of interest. The Analysis of Variance (ANOVA) with Tukey's multiple comparison adjustment was used for comparisons of more than two independent groups. Dichotomous data were compared using the chi-square test with the Yates correction or Fisher's exact test when appropriate. The Kolmogorov-Smirnov test (KS-test) was used to determine if the distribution of the datasets differed significantly. For progression free survival (PFS) analysis, the survival curves were estimated using the Kaplan-Meier method with the log-rank test to examine the statistically significant differences between study groups. For gene analysis, the FDR adjusted Student t-test was used to identify the "winner genes" then followed by the complete linkage cluster analysis based on 1-Spearman correlation. Statistical analyses were performed using R or GraphPad Prism. All P values reported were 2-sided.

Example 2: Reduced Tumor Lymphocytic Infiltration in the Residual Disease (RD) of Post-Neoadjuvant Chemotherapy (NAC) Triple-Negative Breast Cancers (TNBC) is Associated with Ras/MAPK Activation and Poorer Survival Background: Tumor-infiltrating lymphocytes (TILs) are associated with improved prognosis in TNBCs, with several retrospective analyses demonstrating that TNBCs with high baseline TILs have higher rates of pathologic complete response (pCR) to NAC. Moreover, the TIL burden in the RD of patients who do not achieve pCR to NAC is also correlated with prognosis. However, insight into the molecular pathways in TNBC which modulate heterogeneity in host anti-tumor immune responses is lacking. To address this gap in knowledge, TILs were analyzed retrospectively in a cohort of clinically and molecularly characterized TNBCs with RD after NAC.

Methods: TILs were scored in H&E stained slides by expert pathologists in the post-treatment tumors of 92 NAC-treated TNBC patients with RD at the time of resection and in 44 matched baseline diagnostic biopsies. Genomic alterations in the RD were assayed using targeted next-generation sequencing (tNGS) while selected transcriptional signatures were evaluated by NanoString as previously published (Balko et al, Cancer Discovery 2014). Differences in pre- and post-NAC TILs were compared between tumors harboring alterations in cell cycle, PI3K/mTOR, growth factor receptors, Ras/MAPK and DNA repair pathways. Associations of TILs with transcriptional signatures were also tested.

Results: A strong positive association of TILs in NAC-treated specimens was observed with RFS (coxPH p=0.0001, relative risk reduction of 3.4% for each % of TILs) and OS (p=0.0016; relative risk reduction of 2.8% for each % of TILs). In multivariate analysis with stage, age, node status and RD tumor cellularity, TILs in the post-NAC disease remained a significant predictor of RFS and OS (p=0.0008 and p=0.007, respectively). TILs tended to decrease with NAC in paired samples, although this decrease was not statistically significant (p=0.07).

Genetic alterations in the Ras/MAPK (amplifications in KRAS, BRAF, RAF1 and truncations in NF1) and cell cycle pathway (alterations in CCND1-3, CDK4, CDK6, CCNE1, RB, AURKA and CDKN2A) were associated with lower TILs in RD (p=0.005 and p=0.05, respectively). A significant inverse linear correlation was detected between a transcriptional signature of Ras/MAPK activation (Pratilas et al, PNAS 2009) and TILs in the RD (Spearman's r=−0.42; p=0.00028). Total number of alterations of likely functional significance detected by tNGS showed no association with TILs, suggesting that the association of Ras/MAPK deregulation and cell cycle alterations with TILs may be a pathway-specific effect.

In TNBC cell lines, chemical inhibition of MEK transcriptionally up-regulated MHC-I and MHC-II molecules, while simultaneously down-regulating mRNA expression of the immune checkpoint inhibitor PD-L1 (MDA-231 p=0.00002, BT549 p=0.0003, and SUM159PT p=0.009). In vivo experiments confirming these associations are underway.

Conclusions: The data suggest a strong correlation of Ras/MAPK pathway activation with immune-evasion and outcome in TNBC. With additional mechanistic understanding, rational design of clinical trials combining MEK inhibitors with PD-L1 antibodies in TNBC may be warranted.

Example 3: Preliminary Data for Use of Tumor Membrane-Specific HLA-DR Expression as a Biomarker of Response to PD-1/PD-L1 Directed Therapy Goal: To determine the rate of prediction of tumor cells expressing HLA-DR on response to PD-1/PD-L1 directed therapy.

Methods: 12 sections from excisional biopsies or surgical resections of melanoma were immune-stained for HLA-DR (TAL-1B5, commercially available for research from multiple vendors). These 12 sections represented 11 patients; 5 responders to anti-PD-1/PD-L1 therapy and 6 non-responders. Two samples were from sequential biopsies, one from prior to a clinical response, and one upon acquisition of resistance (relapse) on therapy.

Tumor sections were stained overnight at 4 C at a 1:1000 dilution. Antigen retrieval was performed using Citrate Buffer (pH6) using a Biocare Dechloaking Chamber. The Visualization System utilized was Envision-Mouse using DAB chromogen and counterstained with Hematoxylin.

Figure 15A:
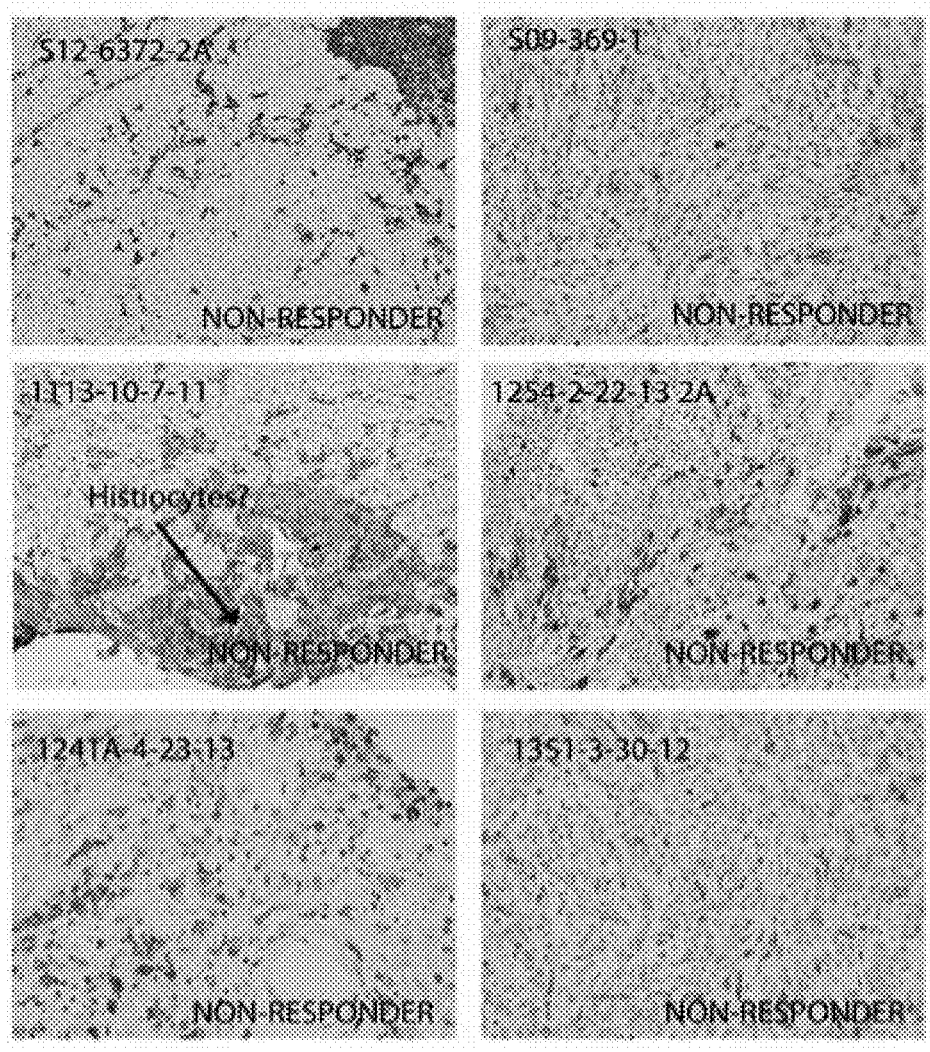
FIGS. 15A-B show images illustrating membrane staining of (A) non-responders and (B) responders.
Figure 15B:
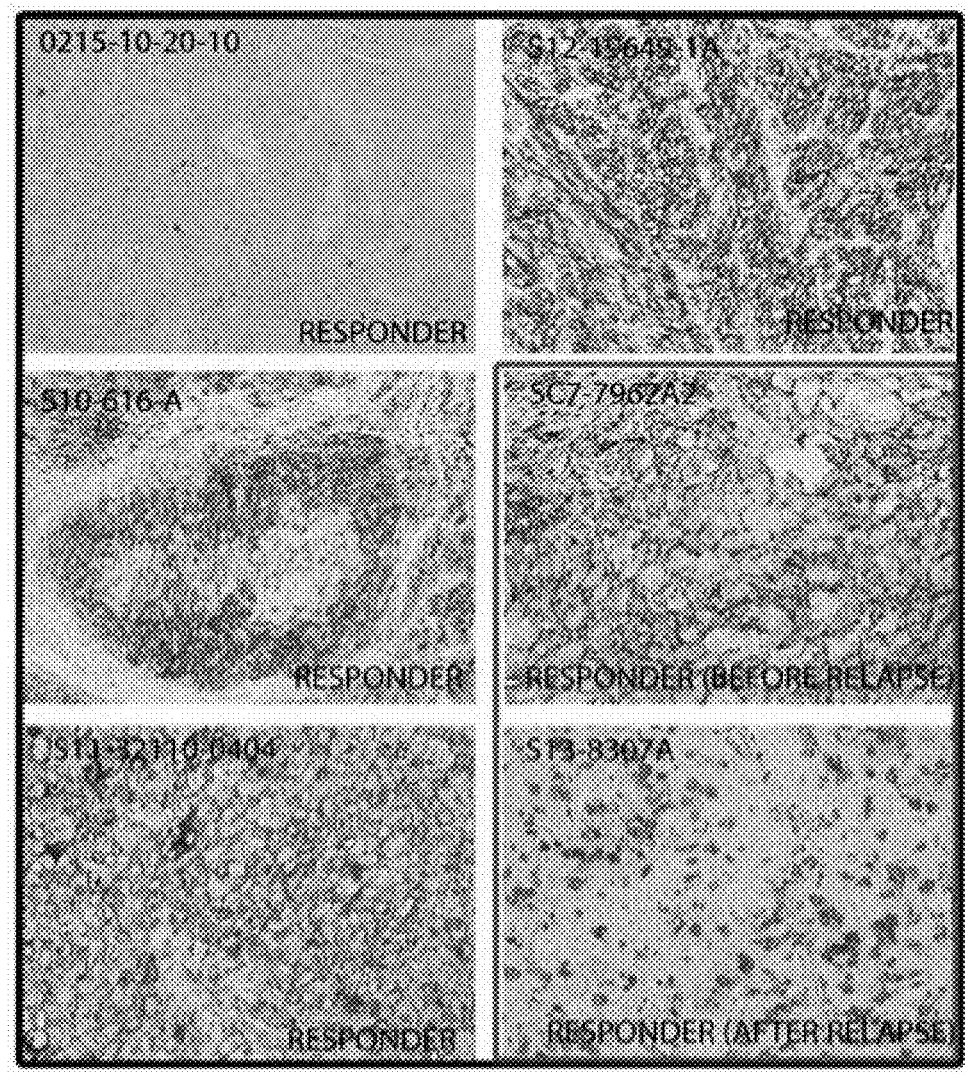

Results: Of 6 non-responders, 0/6 exhibited conclusive tumor-specific membrane staining of HLA-DR (FIG. 15A). One sample (1113-10-7-11) had regional edge cells that stained positive, but were considered likely to be histiocytes and not tumor cells by the pathologist. Of 5 responders, 4/5 had high membrane specific staining of HLA-DR on what appear to be tumor cells (FIG. 15B). Dual staining for melanoma-specific markers are being conducted to confirm the staining pattern. Of note, the one responder sample that was negative for HLA-DR (0215-10-20-10) was from a previous resection several years before therapy and may not be representative of the on-therapy disease. Analysis of sequential samples (prior to response[SC7-7962A2], and after relapse on therapy [S13-8307A]) suggested loss of HLA-DR on the tumor cells that coincided with acquired resistance.

Conclusion: HLA-DR expression on the tumor seems to be a useful biomarker for prediction of response to PD-1/PD-L1 targeted therapy.

Example 4

Figure 16:
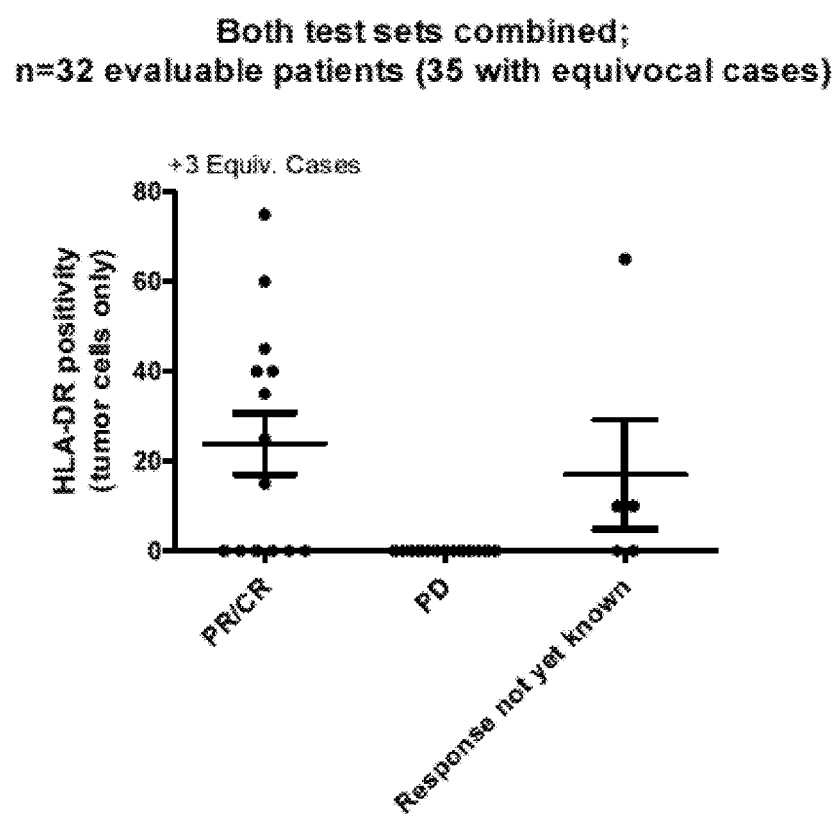
FIG. 16 shows a graph illustrating patient classification by clinical response to targeted immunotherapy. PR and CR refer to partial and complete response, and PD refers to progressive disease.

Formalin fixed paraffin embedded melanoma tumor sections were stained with anti-HLA-DR antibody and anti-SOX10 antibody and reviewed by a pathologist for dual positive tumor cells. Two sample sets were stained independently comprising a total of 35 patients. Patients were then classified by their clinical response to targeted immunotherapy, where known. 32 patients were evaluable, with 3 additional considered equivocal due to uncharacteristic features of HLA-DR staining or lack of SOX10 staining in the perceived tumor region (FIG. 16). PR and CR refer to partial and complete response, and PD refers to progressive disease.

Example 5: Melanoma-Specific MHC-II Expression Predicts Response to α-PD-1 Therapy Background αPD-1 therapy yields objective clinical responses in 30-40% of advanced melanoma (MEL) patients. While promising, many patients do not benefit clinically. As such, predictive biomarkers to guide patient selection are needed. A number of predictive biomarkers have been suggested in the literature, including tumor or immune cell expression of PD-L1, identification of neo-antigens through next generation sequencing techniques, and T-cell receptor sequencing. While quite promising, these assays are technically challenging and require specialized tissue processing or bioinformatics.

Methods. MHC-I/II mRNA was profiled across 60 MEL cell lines. The transcriptional characteristics of MHC-II+ cell lines were analyzed by Gene Set Analysis. Cell surface expression of MHC-I and MHC-II was confirmed by flow cytometry (FC) in a subset of cell lines under basal and stimulated (IFNγ) conditions. In 26 tumor samples from αPD-1 treated MEL patients, immunohistochemistry (IHC) was performed for HLA-DR (MHC-II) or HLA-A (MHC-I), SOX10, CD4 and CD8. IHC results were correlated with response and progression-free survival (PFS).

Results. MHC-1 mRNA was expressed in all cell lines while MHC-II expression was bimodal (60% positive). MHC-II$^+$ cell lines had transcriptional signatures of the PD-1 signaling, allograft rejection, and T-cell receptor signaling. By FC, MHC-II$^+$ (mRNA) cell lines were constitutive and inducible (IFNγ stimulation) for HLA-DR while MHC-II$^-$ cells did not express or induce HLA-DR. In contrast, all tested cell lines significantly upregulated PD-L1 with IFNγ stimulation. Of 26 patients treated with αPD-1, 10 were MHC-II$^+$. All 10 MHC-II$^+$ (100%) patients had partial, complete, or mixed responses (MR), while only 7/16 (44%) of MHC-II$^-$ patients benefited (Fisher's exact p=0.004). Excluding MR patients (n=2), median PFS for MHC-II$^+$ was 728 days, while the median PFS for MHC-II$^-$ tumors was 98 days (log-rank p=0.01). MHC-II$^+$ tumors had enhanced CD4 and CD8 infiltrate (Pearson's correlation p=0.000002 and p=0.03, respectively). MHC-I positivity was ubiquitous and not associated with response.

Conclusions. A subset of MEL demonstrates an MHC-II signature that correlates with αPD-1 response and enhanced CD4/CD8 T-cell infiltrate. Without wishing to be bound theory, this is believed to indicate that tumor antigen presentation (MHC-II expression) is a requirement of αPD-1 benefit, and presence of these cell surface markers is predictive benefit. MHC-II+ tumors can be robustly identified by routine melanoma-specific IHC for HLA-DR to guide patient selection. Combining HLA-DR IHC with other biomarkers, including PD-L1 expression may further improve patient selection.

All publications, patents, and patent applications mentioned in this specification are herein incorporated by reference to the same extent as if each individual publication, patent, or patent application was specifically and individually indicated to be incorporated by reference, including the references set forth in the following list:

1. Topalian, S. L., et al. Safety, activity, and immune correlates of anti-PD-1 antibody in cancer. The New England journal of medicine 366, 2443-2454 (2012).
2. Hamid, O., et al. Safety and Tumor Responses with Lambrolizumab (Anti-PD-1) in Melanoma. The New England journal of medicine 369, 134-144 (2013).
3. Herbst, R. S., et al. Predictive correlates of response to the anti-PD-L1 antibody MPDL3280A in cancer patients. Nature 515, 563-567 (2014).
4. Robert, C., et al. Nivolumab in Previously Untreated Melanoma without BRAF Mutation. The New England journal of medicine (2014).
5. Robert, C., et al. Anti-programmed-death-receptor-1 treatment with pembrolizumab in ipilimumab-refractory advanced melanoma: a randomised dose-comparison cohort of a phase 1 trial. Lancet (2014).
6. Robert, C., et al. Pembrolizumab versus Ipilimumab in Advanced Melanoma. The New England journal of medicine (2015).
7. Rizvi, N. A., et al. Activity and safety of nivolumab, an anti-PD-1 immune checkpoint inhibitor, for patients with advanced, refractory squamous non-small-cell lung cancer (CheckMate 063): a phase 2, single-arm trial. The lancet oncology 16, 257-265 (2015).
8. Garon, E. B., et al. Pembrolizumab for the Treatment of Non-Small-Cell Lung Cancer. The New England journal of medicine (2015).
9. Gettinger, S. N., et al. Overall Survival and Long-Term Safety of Nivolumab (Anti-Programmed Death 1 Antibody, BMS-936558, ONO-4538) in Patients With Previously Treated Advanced Non-Small-Cell Lung Cancer. Journal of clinical oncology: official journal of the American Society of Clinical Oncology (2015).
10. Motzer, R. J., et al. Nivolumab for Metastatic Renal Cell Carcinoma: Results of a Randomized Phase II Trial. Journal of clinical oncology: official journal of the American Society of Clinical Oncology (2014).
11. Powles, T., et al. MPDL3280A (anti-PD-L1) treatment leads to clinical activity in metastatic bladder cancer. Nature 515, 558-562 (2014).
12. Ansell, S. M., et al. PD-1 Blockade with Nivolumab in Relapsed or Refractory Hodgkin's Lymphoma. The New England journal of medicine (2014).
13. Nanda, R., Chow L Q, Dees E C, Berger R, Gupta S, et al. A phase Ib study of pembrolizumab (MK-3475) in patients with advanced triple-negative breast cancer. in San Antonio Breast Cancer Symposium (2014).
14. Seiwert, T. Y., Burtness B, Weiss J, Gluck I, Eder J P, et al. A phase Ib study of MK-3475 in patients with human papillomavirus (HPV)-associated and non-HPV-associated head and neck (H/N) cancer. Journal of clinical oncology: official journal of the American Society of Clinical Oncology 32, 6011 (2014).
15. Brahmer, J. R., et al. Phase I study of single-agent anti-programmed death-1 (MDX-1106) in refractory solid tumors: safety, clinical activity, pharmacodynamics, and immunologic correlates. Journal of clinical oncology: official journal of the American Society of Clinical Oncology 28, 3167-3175 (2010).
16. Snyder, A., et al. Genetic Basis for Clinical Response to CTLA-4 Blockade in Melanoma. The New England journal of medicine (2014).
17. Yadav, M., et al. Predicting immunogenic tumour mutations by combining mass spectrometry and exome sequencing. Nature 515, 572-576 (2014).
18. Tumeh, P. C., et al. PD-1 blockade induces responses by inhibiting adaptive immune resistance. Nature 515, 568-571 (2014).
19. Spranger, S., Bao, R. & Gajewski, T. F. Melanoma-intrinsic beta-catenin signalling prevents anti-tumour immunity. Nature 523, 231-235 (2015).
20. Mellman, I., Coukos, G. & Dranoff, G. Cancer immunotherapy comes of age. Nature 480, 480-489 (2011).
21. Mikucki, M. E., et al. Non-redundant requirement for CXCR3 signalling during tumoricidal T-cell trafficking across tumour vascular checkpoints. Nat Commun 6, 7458 (2015).
22. Garrido, F., Cabrera, T. & Aptsiauri, N. "Hard" and "soft" lesions underlying the HLA class I alterations in cancer cells: implications for immunotherapy. Int J Cancer 127, 249-256 (2010).
23. Warabi, M., Kitagawa, M. & Hirokawa, K. Loss of MHC class II expression is associated with a decrease of tumor-infiltrating T cells and an increase of metastatic potential of colorectal cancer: immunohistological and histopathological analyses as compared with normal colonic mucosa and adenomas. Pathol Res Pract 196, 807-815 (2000).
24. Bernsen, M. R., et al. On the biological relevance of MHC class II and B7 expression by tumour cells in melanoma metastases. Br J Cancer 88, 424-431 (2003).
25. Oldford, S. A., et al. Tumor cell expression of HLA-DM associates with a Th1 profile and predicts improved survival in breast carcinoma patients. Int Immunol 18, 1591-1602 (2006).
26. Degenhardt, Y., et al. Distinct MHC gene expression patterns during progression of melanoma. Genes Chromosomes Cancer 49, 144-154 (2010).
27. Pollack, M. S., Heagney, S. D., Livingston, P. O. & Fogh, J. HLA-A, B, C and DR alloantigen expression on forty-six cultured human tumor cell lines. Journal of the National Cancer Institute 66, 1003-1012 (1981).
28. Barbieri, G., Rimini, E. & Costa, M. A. Effects of human leukocyte antigen (HLA)-DR engagement on melanoma cells. International journal of oncology 38, 1589-1595 (2011).
29. Colloby, P. S., West, K. P. & Fletcher, A. Is poor prognosis really related to HLA-DR expression by malignant melanoma cells? Histopathology 20, 411-416 (1992).
30. Chornoguz, O., Gapeev, A., O'Neill, M. C. & Ostrand-Rosenberg, S. Major histocompatibility complex class II+ invariant chain negative breast cancer cells present unique peptides that activate tumor-specific T cells from breast cancer patients. Mol Cell Proteomics 11, 1457-1467 (2012).
31. Londei, M., Lamb, J. R., Bottazzo, G. F. & Feldmann, M. Epithelial cells expressing aberrant MHC class II determinants can present antigen to cloned human T cells. Nature 312, 639-641 (1984).
32. Meazza, R., Comes, A., Orengo, A. M., Ferrini, S. & Accolla, R. S. Tumor rejection by gene transfer of the MHC class II transactivator in murine mammary adenocarcinoma cells. Eur J Immunol 33, 1183-1192 (2003).
33. Rizvi, N. A., et al. Cancer immunology. Mutational landscape determines sensitivity to PD-1 blockade in non-small cell lung cancer. Science 348, 124-128 (2015).
34. Wellbrock, C., et al. STAT5 contributes to interferon resistance of melanoma cells. Curr Biol 15, 1629-1639 (2005).
35. Lee, Y. S., Kim, S. H., Cho, J. A. & Kim, C. W. Introduction of the CIITA gene into tumor cells produces exosomes with enhanced anti-tumor effects. Exp Mol Med 43, 281-290 (2011).
36. Joseph, R. W., et al. Correlation of NRAS mutations with clinical response to high-dose IL-2 in patients with advanced melanoma. J Immunother 35, 66-72 (2012).
37. Johnson, D. B., et al. Impact of NRAS Mutations for Patients with Advanced Melanoma Treated with Immune Therapies. Cancer immunology research 3, 288-295 (2015).
38. Loor, F. & Kindred, B. Differentiation of T-cell precursors in nude mice demonstrated by immunofluorescence of T-cell membrane markers. J Exp Med 138, 1044-1055 (1973).
39. Rodriguez, T., et al. Patterns of constitutive and IFN-gamma inducible expression of HLA class II molecules in human melanoma cell lines. Immunogenetics 59, 123-133 (2007).
40. Wolchok, J. D., et al. Nivolumab plus Ipilimumab in Advanced Melanoma. The New England journal of medicine (2013).
41. Postow, M. A., et al. Nivolumab and Ipilimumab versus Ipilimumab in Untreated Melanoma. The New England journal of medicine (2015).
42. Larkin, J., et al. Combined Nivolumab and Ipilimumab or Monotherapy in Untreated Melanoma. N Engl J Med 373, 23-34 (2015).
43. Benjamini, Y. & Hochberg, Y. Controlling the False Discovery Rate: A Practical and Powerful Approach to Multiple Testing. Journal of the Royal Statistical Society. Series B (Methodological) 57, 289-300 (1995).
44. Efron, B. & Tibshirani, R. On testing the significance of sets of genes. Annals of Applied Statistics 1, 107-129 (2007).

45. Balko, J. M., et al. Profiling of residual breast cancers after neoadjuvant chemotherapy identifies DUSP4 deficiency as a mechanism of drug resistance. Nat Med 18, 1052-1059 (2012).
46. Balko, J. M., et al. Activation of MAPK pathways due to DUSP4 loss promotes cancer stem cell-like phenotypes in basal-like breast cancer. Cancer Res (2013).
47. Barretina, J., et al. The Cancer Cell Line Encyclopedia enables predictive modelling of anticancer drug sensitivity. Nature 483, 603-607 (2012).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of detecting cell membrane expression of an MHC molecule in a subject suspected of having cancer and being in need of immunotherapy, comprising:
    (a) obtaining a tumor cell sample from the subject;
    (b) detecting cell membrane expression of the MHC molecule by contacting the tumor cell sample with an antibody targeting the MHC molecule and detecting binding between the MHC molecule and the antibody;
    (c) detecting a cancer specific marker on the tumor cell sample; and
    (d) administering a therapeutically effective amount of nivolumab, pembrolizumab, MPDL3280a, or anti-LAG3 to the subject having a tumor cell sample with increased cell membrane expression of the MHC molecule relative to a control as detected in step (b) and positive cancer specific marker staining as detected in step (c);
    wherein expression of the MHC molecule is measured using at least one method selected from the group consisting of immunohistochemistry, immunofluorescence, flow cytometry, mass-spectroscopy, or combinations thereof.

2. The method of claim 1, wherein the MHC molecule is selected from HLA-A, HLA-B, HLA-C, HLA-DO, HLA-DM, HLA-DR, HLA-DP, HLA-DQ, and HLA-DX.

3. The method of claim 1, wherein the MHC molecule is HLA-DR.

4. The method of claim 3, and further comprising detecting expression of a marker selected from the group consisting of: HLA-A, HLA-B, HLA-C, PD-1, PD-L1, CD8, CD4, CIITA, Foxp3, LAG3, TIM3, Ox40, Ox40L, 41BB, VISTA, Interferon gamma, Granzyme B, CTLA-4, and SOX-10.

5. The method of claim 1, wherein the cancer-specific marker is a melanoma-specific marker.

6. The method of claim 5, wherein the melanoma-specific marker is SOX-10.

7. The method of claim 1, wherein the tumor cell sample is from a cancer selected from: melanoma, lung, ovarian, renal, colorectal, head and neck, bladder, endometrial, pancreatic, breast, and liver cancer.

8. The method of claim 1, wherein the tumor cell sample is formalin-fixed.

9. The method of claim 1, wherein the tumor cell sample is not a frozen tissue sample.

10. The method of claim 1, and further comprising administration of a MEK, epigenetic DNA methyltransferase, or histone deacetylase inhibitor to the subject.

* * * * *